US008285396B2

(12) United States Patent
Bulkes et al.

(10) Patent No.: US 8,285,396 B2
(45) Date of Patent: Oct. 9, 2012

(54) MRI COMPATIBLE ELECTRICAL LEAD FOR AN IMPLANTED ELECTRONIC MEDICAL DEVICE

(75) Inventors: Cherik Bulkes, Sussex, WI (US); Stephen Denker, Mequon, WI (US)

(73) Assignee: Kenergy, Inc., Mequon, WI (US)

( * ) Notice: Subject to any disclaimer, the term of this patent is extended or adjusted under 35 U.S.C. 154(b) by 355 days.

(21) Appl. No.: 12/651,597

(22) Filed: Jan. 4, 2010

(65) Prior Publication Data

US 2010/0174348 A1 Jul. 8, 2010

Related U.S. Application Data

(60) Provisional application No. 61/142,401, filed on Jan. 5, 2009.

(51) Int. Cl.
*A61N 1/05* (2006.01)
(52) U.S. Cl. ........................................ 607/116; 607/115
(58) Field of Classification Search ......... 607/2, 115–119
See application file for complete search history.

(56) References Cited

U.S. PATENT DOCUMENTS

| 2,966,640 | A | 12/1960 | Eiland, Jr. |
| 5,217,010 | A | 6/1993 | Tsitlik et al. |
| 6,713,671 | B1 | 3/2004 | Wang et al. |
| 6,930,242 | B1 | 8/2005 | Helfer et al. |
| 7,363,090 | B2 | 4/2008 | Halperin et al. |
| 7,917,213 | B2 | 3/2011 | Bulkes et al. |
| 2003/0036776 | A1 | 2/2003 | Foster et al. |
| 2003/0050557 | A1 | 3/2003 | Susil et al. |
| 2003/0144721 | A1 | 7/2003 | Villaseca et al. |
| 2004/0014355 | A1 | 1/2004 | Osypka et al. |
| 2004/0199069 | A1 | 10/2004 | Connelly et al. |
| 2004/0215300 | A1 | 10/2004 | Verness |
| 2004/0230271 | A1 | 11/2004 | Wang et al. |
| 2006/0212096 | A1 | 9/2006 | Stevenson |
| 2006/0247684 | A1 | 11/2006 | Halperin et al. |
| 2007/0112398 | A1 | 5/2007 | Stevenson et al. |
| 2008/0033497 | A1 | 2/2008 | Bulkes et al. |
| 2008/0051854 | A1 | 2/2008 | Bulkes et al. |
| 2008/0195187 | A1 | 8/2008 | Li et al. |
| 2008/0221638 | A1 | 9/2008 | Wedan et al. |

(Continued)

FOREIGN PATENT DOCUMENTS

WO 2006023700 A 3/2006

(Continued)

*Primary Examiner* — Carl H Layno
*Assistant Examiner* — Paula J Stice
(74) *Attorney, Agent, or Firm* — Quarles & Brady LLP; George E. Haas

(57) ABSTRACT

An electrical lead, for implantation in an animal, is compatible with an MRI scanner. The electrical lead has a first plurality of coiled insulated wires forming an outer layer of conductors that has a first inductance and a first capacitance, which act as a first parallel resonator tuned to a Larmor frequency of tissue in the animal. The lead may have a second plurality of coiled insulated wires forming an inner layer of conductors within the outer layer of conductors. The second plurality of coiled insulated wires has a second inductance and a second capacitance that act as a second parallel resonator tuned to the Larmor frequency. Those parallel resonators mitigate signals at the Larmor frequency from traveling along the respective coil. An electrically conductive layer extends around the inner and/or outer layer of conductors, and a layer of a biologically compatible material forms the electrical lead's exterior surface.

27 Claims, 11 Drawing Sheets

| U.S. PATENT DOCUMENTS | | | | FOREIGN PATENT DOCUMENTS | | |
|---|---|---|---|---|---|---|
| 2008/0243218 A1 | 10/2008 | Bottomley et al. | | WO | 2006093685 A | 9/2006 |
| 2009/0149920 A1* | 6/2009 | Li et al. .......................... 607/63 | | WO | 2006105066 A | 10/2006 |
| 2009/0171421 A1 | 7/2009 | Atalar et al. | | | | |
| 2009/0281592 A1 | 11/2009 | Vase | | | | |

* cited by examiner

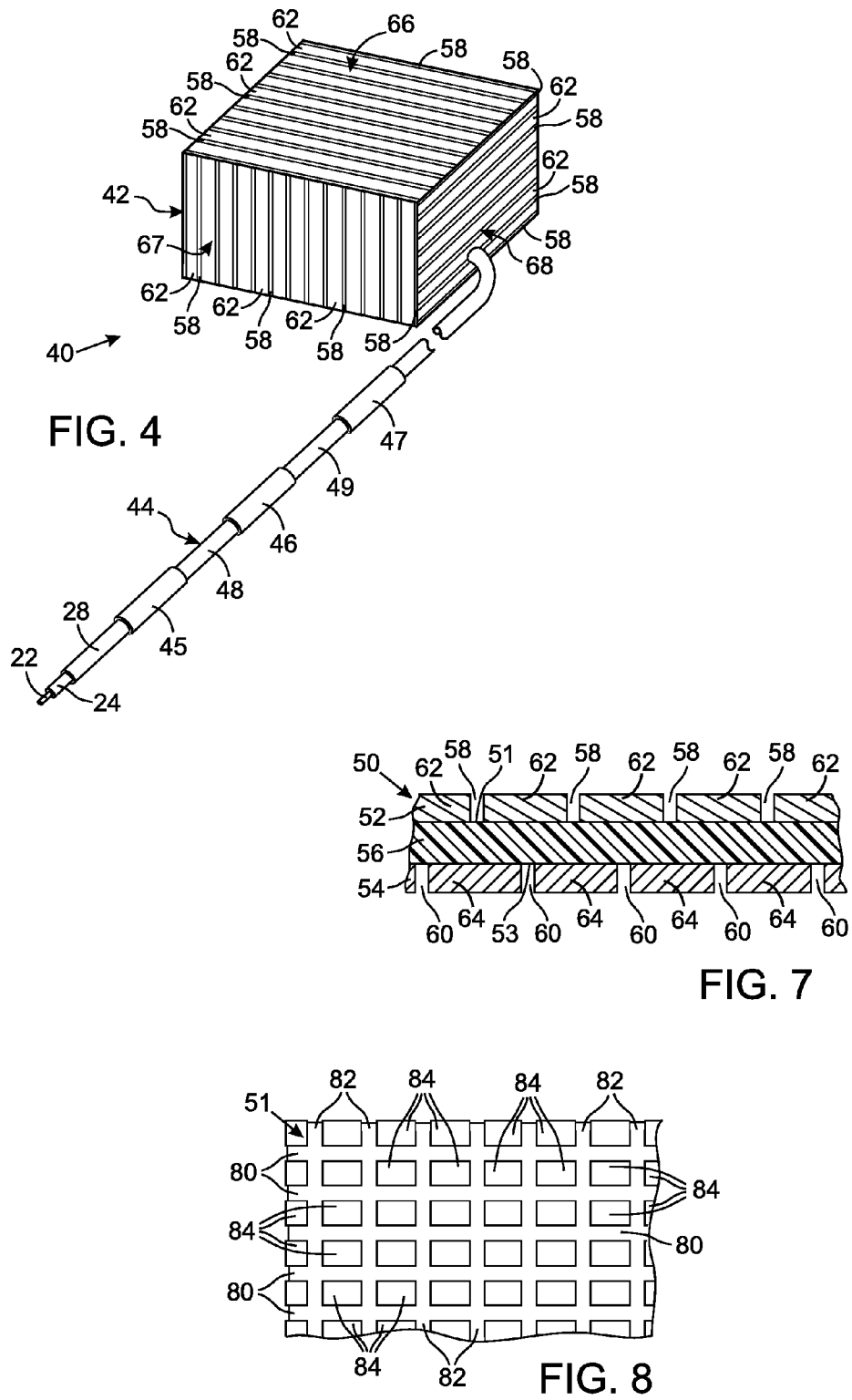

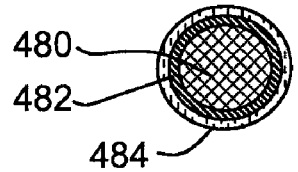
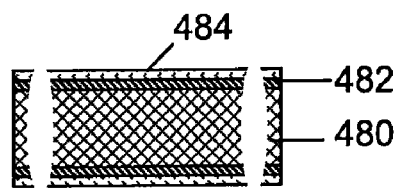
FIG. 11A  FIG. 11B
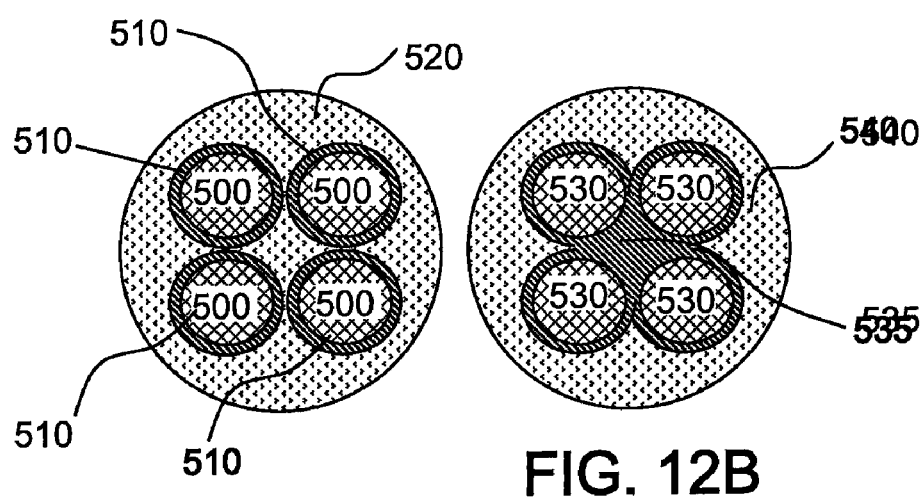
FIG. 12A  FIG. 12B

MRI COMPATIBLE ELECTRICAL LEAD FOR AN IMPLANTED ELECTRONIC MEDICAL DEVICE

CROSS-REFERENCE TO RELATED APPLICATIONS

This application claims benefit of U.S. Provisional Patent Application No. 61/142,401 filed on Jan. 5, 2009.

STATEMENT REGARDING FEDERALLY SPONSORED RESEARCH OR DEVELOPMENT

Not Applicable

BACKGROUND OF THE INVENTION

1. Field of the Invention

The present invention relates implantable electronic medical devices, such as cardiac pacemakers and defibrillators for example, for stimulating tissue of animal for the therapeutic purposes, and such implantable medical devices that are compatible with magnetic resonance imaging (MRI).

2. Description of the Related Art

Numerous medical conditions, such as cardiac and neurological dysfunctions, are treated by an implanted electronic device which provides electrical stimulation to the affected tissue of the animal. These devices have a plurality of metal components, including the generator case and wire leads extending from the case to electrodes in contact with the tissue to be stimulated or monitored.

Magnetic resonance imaging (MRI) is commonly employed to view internal organs of medical patients. To create an image, the patient is placed into very strong static and varying magnetic and radio frequency (RF) fields and thus MRI generally is prohibited for patients with implanted ferromagnetic and or electrically conductive objects. Although it is feasible to minimize and even eliminate the use of ferromagnetic materials in implanted apparatus, electronic devices, such as cardiac pacemakers and defibrillators, require electrically conductive components that are affected by the fields produced by an MRI scanner.

It has been a long-standing goal to make implanted devices MRI compatible so that this imaging modality can be used with patients having those devices. There are several reasons for achieving this goal. First, incompatible implant components induce susceptibility difference, which destroys DC magnetic field homogeneity, thereby affecting the imaging performance of the magnetic resonance (MR) scanner. Second, conductive materials present an opportunity for eddy currents to form, which currents generate heat that adversely affects patient safety and degrade the scanner performance by field distortion. Third, the MRI fields may ruin the implanted device. Fourth, the incompatible implant material can potentially cause serious internal injuries to the patient. Therefore, "MRI compatible" as used herein means that an implanted device and its components do not degrade or distort an MRI image or produce image artifacts that compromise the diagnostic value of an image. In addition, interaction between the implanted device components and the electromagnetic fields produced by the MRI scanner does not result in unsafe heating of the animal, as defined by the United States Food and Drug Administration, because such heating that can burn animal's tissue.

The issue of MRI interaction with electronics of an implanted device has to be considered in an integrated fashion to provide compatibility. Table 1 shows combinations of interactions that are briefly discussed hereinafter.

TABLE 1

| Interactions of Factors Influencing MRI Compatibility of an Implanted Device or Component | | | |
|---|---|---|---|
|  | Patient Safety | Effect on the Implanted Device | Effect on the MR Image |
| DC Magnetic Fields | I | II | III |
| Gradient Magnetic Fields | IV | V | VI |
| RF Fields | VII | VIII | IX |

I. Any ferromagnetic material inside the implanted device exposed to the MRI fields experiences a force and a torque, the amount of which depends on the shape, dimensions, and amount of ferromagnetic material. The forces are greatest in areas where there is a gradient in the magnetic field, e.g. upon entering a MRI system. Obviously the surrounding tissue adjacent the implantable device will be damaged in this case and the health of the patient will be compromised. In addition, metallic components can become hot and burn the patient.

II. Due to MRI field induced torque and movement of the implant, its components may become disconnected making the device inoperable. Ferrites and other ferromagnetic material in transformer cores, inductors and other electronic components become saturated, thereby jeopardizing the function of the medical device. Heating causes electronic components to operate out of specification.

III. The homogeneity of the magnetic resonance imager's DC magnetic field will be distorted, destroying spectral resolution and geometric uniformity of the image. The inhomogeneous field also results in rapid de-phasing of the signal inside the excited volume of the patient. The resultant image shows a distorted view of the patient's anatomy.

Even if the implanted device does not contain any ferromagnetic materials, the magnetic susceptibility of the device may be different than that of the surrounding tissue, giving rise to local distortion and signal dropouts in the image, close to the device. This is especially true for pulse sequences that are sensitive to phase, like echo planar imaging IV. Switching field gradients create large eddy currents, at frequencies up to a few kilohertz, in the metallic housing of an implantable device and any metallic part that forms a loop, such as cables forming a loop. These eddy currents make the device move with the same frequency as the leading and trailing edges of gradient pulses. This movement can be unsafe for the surrounding tissue. The associated eddy current pattern creates local pulsating E-fields, in addition to the E-field generated by the MRI scanner's gradient coil, which can stimulate the patient's nerves. Resultant muscle twitching can be so intense as to be painful.

V. The eddy currents may be strong enough to damage electronic circuits and destroy the implanted device. The pulsating forces on the device may disconnect components.

VI. The eddy currents affect the rise time of the MRI gradient pulses, and therefore affect the minimum obtainable echo time, necessary for many pulse sequences. The eddy currents also locally distort the linearity of the gradient fields and de-phase the spin system, resulting in image distortion and signal dropouts. Phase and frequency encoding of the signal strongly depends on the linearity of the gradients.

VII. The RF field interacts with any metallic part in the device, be it either in the form of a loop, which results in B-field coupling, or a straight conductor, which results in E-field coupling. The B-field component of the RF field can induce currents and voltages in conducting loops. The amplitude depends on the impedance of the loop at the RF frequency, and the size of the loop. An example may be two coaxial cables that form a loop together. Such a loop may have high impedance at DC due to the insulating outer shell of the coax, but the distance between the cables at the crossover point may be equivalent to just the right amount of capacitance to make the loop resonant at the RF frequency.

The E-field component of the RF field will induce voltages and currents in straight conductors, like a single cable for example. The amplitude of the induced voltages and currents depends on the phase length of the conductor, or path, at the associated radio frequency and the conductivity of the conductor.

The induced voltages and currents create locally very strong E-fields that can burn the patient.

Non-metallic implantable devices do not have these issues, but can still distort the uniformity of the RF field if the permittivity of the device is different than that of the surrounding tissue. This distortion is especially strong at radio frequencies above 100 MHz.

VIII. Localized high voltages and currents in the medical device may cause components to fail either due to high voltage arcing, or due to dissipated power and heat. This includes connections that become unsoldered due to the heat. The device may generate pulsed voltages at unwanted times and locations in the leads of a cardiac pacemaker.

IX. Local distortion of the uniformity of the B-field component of the RF field will give rise to flip angle variation and creates contrast and signal-to-noise ratio (SNR) inhomogeneity. The specific absorption rate, which is defined as the RF power absorbed per unit of mass of an object, can exceed legal limits. If the specific absorption rate exceeds legal limits, images cannot be made using magnetic resonance scanners.

From a fundamental physical perspective, it is useful to examine the conductivity of wires at high frequencies of MRI. As frequencies increase, conduction begins to move from an equal distribution through the conductor cross section toward existence almost exclusively near the surface. Depending on the conductor bulk resistivity, at sufficiently high frequency all the RF current is flowing within a very small thickness at the surface. Lower bulk resistivity results in shallower electromagnetic (EM) skin depths in the conductor.

For a solid wire, the current concentrates on the outer surface. For this reason, when EM skin depth is shallow, the solid conductor can be replaced with a hollow tube with no perceivable loss of performance. Choice of a plating material can degrade performance (increase attenuation) if its bulk resistivity is greater than that of the body of the wire. If such a conductor is placed inside the E field of an MRI RF transmit coil, there will be RF energy deposition in the tissue surrounding the wire resulting in elevated temperatures that may result in physical injury to the patient. There also may be current flowing into the tissue at tips of the wire.

An implantable enclosure with an integrated antenna provides another challenge for MRI compatibility. The antenna may be used for powering the implanted device or for unidirectional or bidirectional communication with an external device.

In general, implanted devices are contained in an electrically conductive container, typically made of metal. This container also serves as an electromagnetic interference (EMI) shield, protecting the contained electronics from external electrical or magnetic noise. Such noise can potentially interfere with the function of the device as it may cause corruption of the physiological data that is being gathered. The signal levels of physiological data tends to be very small, e.g., tens or hundreds of microvolts for neural signals, and one to tens of millivolts for muscle signals. Ambient electrical noise (EMI) field strengths in home, store, office or industrial environments can be anywhere from one volt per meter to hundreds of volts perimeter and set up induced noise levels in the body that can easily be many times larger than the signal of interest.

As a consequence a standard method is to shield the sensitive electronics with a conductive enclosure, thus presenting a Faraday cage or shield. A disadvantage of this method is that in order for a power or communication antenna to work, the antenna has to be positioned outside of that enclosure, as an internal antenna would not be able to receive or transmit effectively through the Faraday shield.

Therefore, there is a need for providing a solution to this problem so that an implanted antenna module for the purposes of power and data transfer/communication for electrical sensing is MRI compatible.

SUMMARY OF THE INVENTION

The present invention is directed toward an electrical lead for a medical device that is adapted for implantation in an animal and that is compatible with a magnetic resonance imaging (MRI) scanner which responds to signals at a Larmor frequency of tissue in the animal. The electrical lead comprises a first coil that includes at least one first insulated conductor wound along a length of the lead. The first coil has a first inductance and a first capacitance, wherein the first inductance and the first capacitance cause the first coil to act as a first parallel resonator tuned to the Larmor frequency. The first parallel resonator mitigates signals at the Larmor frequency that otherwise would travel along the first coil.

An electrically conductive layer extends around the first coil. The electrically conductive layer serves to dissipate or quench radio frequency energy that enters the electrical lead.

As an additional aspect, the electrical lead has a second coil which includes at least one second insulated conductor wound along a length of the lead. The second coil has a second inductance and a second capacitance that cause the second coil to act as a second parallel resonator tuned to the Larmor frequency. The second parallel resonator mitigates signals at the Larmor frequency that otherwise would travel along the second coil. The first coil and second coil may be wound in the same or opposite directions along the length of the electrical lead.

In another aspect a outer layer of a biologically compatible material encases the first coil, second coil and the electrically conductive layer, and forms an exterior surface of the electrical lead.

BRIEF DESCRIPTION OF DRAWINGS

FIG. 4 illustrates an electrical lead extending from a medical device housing to stimulation electrodes;

FIG. 7 is a cross section through a wall of a medical device housing showing slots in conductive layers that prevent formation of gradient eddy currents;

FIG. 8 is a plane view of an alternative configuration of slots in the surface of the medical device housing;

FIG. 11A is a schematic of the cross sectional view of an electrical lead assembly;

FIG. 11B is a longitudinal view of the electrical lead assembly;

FIG. 12A is a schematic of the cross sectional view of the lead assembly with each conducting wire individually covered by a medium conductivity material;

FIG. 12B is a cross sectional view of the lead assembly wherein the entire assembly is coated by medium conductivity material;

DETAILED DESCRIPTION OF THE INVENTION

Figure 1:
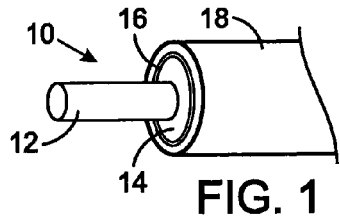
FIG. 1 is an isometric view of a conventional coaxial cable that is used as a medical device lead.

The present technique for MRI compatibility of an implanted electronic medical device considers several effects of direct current (DC) magnetic fields, gradient magnetic fields, and RF fields on patient safety, the implanted device and the MRI scanner. As a consequence, the medical device incorporates one or more mechanisms that offer high impedance to currents induced by the MRI electromagnetic fields or prevent such currents from forming in the first place. These mechanisms comprise non-ferromagnetic components which have a magnetic susceptibility close to that of the surrounding tissue; electrical leads with traps for MRI induced currents, and a housing formed by a plurality of electrically conductive segments that combine to provide RF shielding of internal circuit while not providing large enough areas for formation of eddy currents. As used herein, a "trap" is a circuit element that either blocks current induced by the MRI fields or significantly attenuates those currents to a level at which the current does not cause an adverse effect to the animal being scanned.

The cable traps are placed along the cable to provide high impedance to radio frequency currents induced in the cable while presenting low impedance to direct current of stimulation pulses produced by the medical device. Such traps provide sufficiently high impedance, reactance and/or resistance, to prevent induced current from forming during MRI radio frequency pulses in the 1-500 MHz range.

A terminating element at the lead to stimulator circuit interface, which provides high impedance at the gradient rise time frequency (e.g. 1-10 KHz), but low impedance at the frequency of the generated pulses or sensed cardiac signal, eliminates currents induced on the lead by the E-field produced by the gradient coils in the MRI system. One embodiment employs parallel resonant networks, such as bazooka baluns, to prevent standing waves on the shield of the cable. With a balun configuration, one may include small, rigid stress relief points along the lead at pre-determined distances since a device lead, for example, a pacemaker lead, may make several turns and loops. The reason for putting rigid pieces in is to keep the resonance frequency of the balun constant. In a flexible structure the frequency of the balun would move around too much, especially if it is a self resonant structure. As an alternative to a balun, at least one PIN diode is placed along the cable and selectively forward and reverse biased by a DC control voltage to act as a switch. The PIN diode is rendered conductive during stimulation pulses produced by the medical device and is non-conductive at other times. A micro electro-mechanical system (MEMS) is another type of switch that can be used. The DC leads also need to present high impedance at the RF frequency, which can be accomplished via chokes, or resistors, if the diode or MEMS switch uses low current.

In an embodiment, lead design is based on transmission line type architecture with a characteristic phase rotation along the length of the transmission line. The parameters to characterize the lead's electrical characteristic include varying pitch, turn to turn distance, coaxial radial spacing, permittivity of dielectric and number of layers. Having more turns per unit of length increases inductance and capacitance. Increasing turn to turn spacing will decrease parasitic capacitance. Adding a second coaxially wound layer creates a classic coax transmission line topology. The resultant circuit structure resembles a chained LC network, with the primary inductance being in the layers and the capacitance between the layers. In this arrangement, turn to turn capacitance will also be present. The effect of "global" capacitance rather than turn to turn capacitance is enhanced by winding the second layer opposite from the inner layer, i.e., if the inner layer is wound clockwise (CW), then the outer layer is wound counter clockwise (CCW).

The electrical length of the lead is a function of a wavelength of interest which is determined by the velocity of the electromagnetic wave in the animal tissue divided by the frequency of the electromagnetic wave. The velocity is the inverse of the square root of the product of permittivity and permeability of the tissue. Preferably the electrical length of the lead is an odd multiple of a quarter wavelength of interest for a 1.5 Tesla (T) MRI scanner operating at 64 MHz or a 3.0 T MRI scanner operating at 127.7 MHz. The same applies to any other frequency, although 1.5 T and 3.0 T are the primary field strengths for clinical use. It is further designed to be electrically open or high impedance (typically the driven end of the lead) at one end and almost shorted at the other end (typically the stimulating end of the lead). In this context, the term "almost shorted" refers to low impedance of 3-5 ohms at 64 MHz.

In some embodiments that are contemplated in the current invention, special considerations need to be taken to ensure MRI compatibility. These considerations may include avoiding loops in the lead at all times unless the distance at the crossover point between the two ends of the lead forming a loop, is larger than approximately ten lead diameters.

The metallic housing, for the medical device's electronic circuitry, is separated into a plurality of overlapping electrically conductive segments that are insulated from one another. The result is a housing that offers high impedance for signals up to 200 KHz and acts as a continuous shield for RF signals. Since traps are narrow band devices, they need to be tuned to the Larmor frequency of the tissue of the animal being imaged by the MRI scanner. The MRI scanner responds to that Larmor frequency. The RF shielding is due to the capacitance coupling between the electrically conductive segments.

With initial reference to FIG. 1, a conventional coaxial cable 10 includes a center conductor 12 surrounded by a cylindrical enclosure 14 of a suitable dielectric material. A cylindrical electrically conductive shield 16 that surrounds the cylindrical enclosure 14 and is encased in an insulating outer cover 18.

Figure 2:
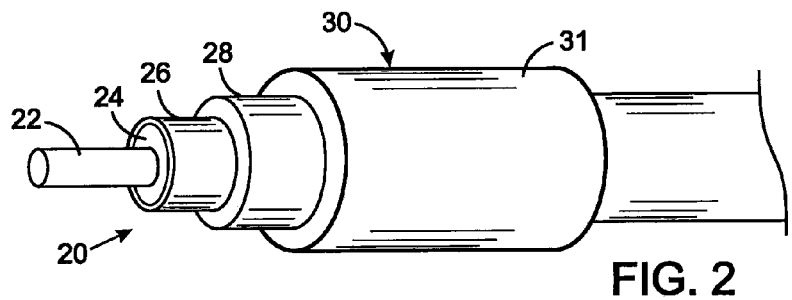
FIG. 2 is an isometric view of a tri-axial cable that has been modified with novel traps to prevent interaction with external RF fields of an MRI scanner.

FIG. 2 illustrates a modification of a standard tri-axial cable according to the present invention to form a coaxial cable with traps for signals induced in the cable by an MRI scanner. The traps impose high impedance to the common mode current induced in the cable by the E-field of an MRI radio frequency body coil. The modified tri-axial cable 20 comprises a central, first conductor 22 surrounded by a first tubular insulator 24 of a conventional dielectric material. A tubular second conductor, or inner shield, 26 extends around the first tubular insulator 24 to form an inner shield and is in turn surrounded by a second tubular insulator 28 of the dielectric material.

A standard tri-axial cable further comprises a tubular outer shield 32 of an electrically conductive material extending around the second tubular insulator 28 for the entire length of the cable. The resultant triaxial structure is encased in an insulating outer cover.

Figure 3:
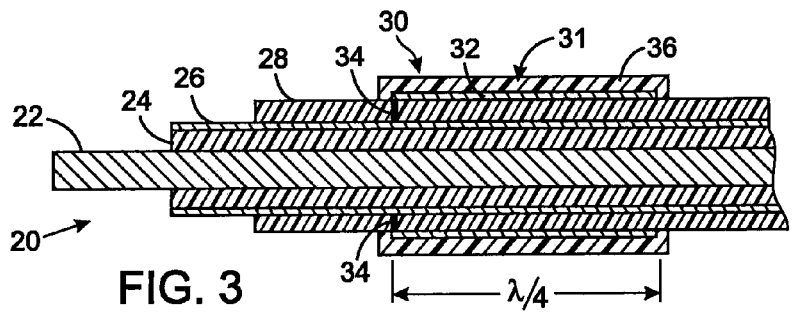
FIG. 3 is a longitudinal cross section of a portion of the tri-axial cable.

The tri-axial cable 20 in FIGS. 2 and 3 is a standard cable tri-axial that has been modified by cutting the tubular outer shield 32 and insulating outer cover 36 into a series of short sections. Those sections form traps 30 for common mode current induced in the cable by an MRI scanner. In the embodiment of FIG. 3, each trap 30 comprises a bazooka balun 31 connected to the remaining cable layers, thereby forming a parallel resonant network connected to a two conductor coaxial cable. The electrically conductive tubular outer shield 32 is cut to a longitudinal length that is identical to one-quarter of the wavelength (λ/4) of an RF frequency for which immunity is desired. This is an RF frequency emitted by the magnetic resonance imaging scanner. As will be described, the cut sections of the outer shield 32 form networks each having an inductor connected in parallel with a capacitor, wherein the LC networks are tuned to different MRI frequencies. One end of each outer shield section is shorted by shunts 34 to the tubular second conductor 26, and the opposite section end is disconnected from the first and second conductors 22 and 26. This forms a standard bazooka balun 31 that is attached to the remaining cable elements 22-28 which function as a coaxial cable. The second tubular insulator 28 now also serves as the outer covering of that coaxial cable. The insulating outer cover 36 encloses the tubular outer shield 32 and preferably has its ends sealed to the second tubular insulator 28 to prevent short circuits.

A bazooka balun may be used for devices for implantation in vasculature of an animal, since the compact diameter of a tri-axial cable occupies relatively small volume of a blood vessel. However, other types of baluns could be used as the traps depending on the intended location of the cable. Examples of other baluns include a cable trap balun, where the cable is looped as a solenoid, and a parallel capacitance connects the grounds before and after the solenoid, thus forming a parallel resonator with high impedance at the frequency of interest. The bridge or lattice balun consisting of a network of two capacitors and two inductors also may be used.

FIG. 4 shows a modified tri-axial cable 20 used as a lead for stimulation electrodes of an implantable medical device 40, such as a cardiac pacemaker or defibrillator. The medical device 40 has electronic circuitry contained in a housing 42 from which a modified tri-axial cable 44 extends. That cable 44 has a plurality of bazooka baluns 45, 46 and 47 with coaxial cable sections 48 and 49 located there between. At the remote end of the cable 44 from the housing 42, the central, first conductor 22 and the second conductor 26 are exposed to form bipolar electrodes for applying DC stimulation pulses to the tissue of the animal in which the device is implanted. Alternatively the central, first conductor 22 and the second conductor 26 can be connected to other forms of electrodes that are adapted for placement in or against particular anatomical features of the animal.

Alternatively, each trap 30 can be formed by a choke placed along the cable at intervals equal to at least a quarter wavelength (λ/4) determined by the Larmor frequency (e.g. 64 MHz at 1.5 T) used by the MRI scanner. The chokes impose high impedance at radio frequencies, but low impedance to DC.

Figure 5:
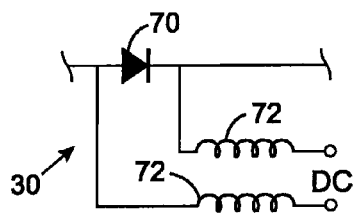
FIG. 5 is a circuit diagram of a second type of trap for the electrical lead.

If a high degree of isolation of the cable to MRI induced currents is desired, PIN diodes 70 can be placed at quarter wavelength intervals along the cable. As shown in FIG. 5, each PIN diode 70 is forward biased by a DC control voltage during a stimulation pulse and reverse biased by that DC control voltage when RF immunity is desired, such as during MRI scan pulses. This embodiment requires additional cable conductors that are decoupled by chokes 72 and consume power from the medical device to bias the PIN diodes during long time periods.

Figure 6:
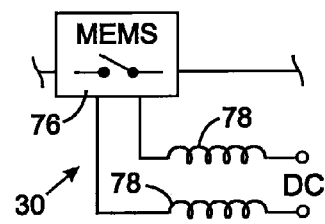
FIG. 6 is a circuit diagram of a third type of trap for the electrical lead.

A further alternative, that provides a high degree of isolation, places a standard micro electro-mechanical system (MEMS) switch 76 at each trap location along the cable as depicted in FIG. 6. The MEMS is a miniaturized RF switch that does not require a large current to close, unlike the large forward bias current required for a PIN diode. However, additional cable conductors and decoupling chokes 78 still are required. Due to the low power consumption of the MEMS, resistive wire may be used to supply the MEMS with DC. The above two solutions require extra wires that now will also need to be decoupled.

In an embodiment, the lead is designed to be a quarter wavelength transmission line at 64 MHz for a 1.5 T MRI scanner or at 127.7 MHz for a 3.0 T MRI scanner. In addition, the quarter wavelength transmission line is shorted at the end, and, therefore, forms high impedance at the other end. Generally, the pitch, layer diameters and wire size are determined by electrical and mechanical design consideration to make the lead mechanically flexible and durable.

Figure 9A:
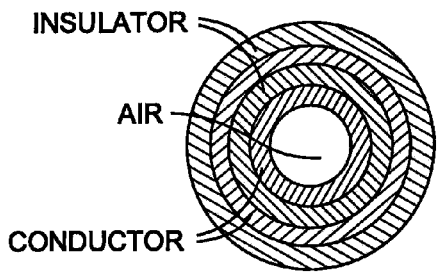
FIG. 9A is a cross sectional view of the electrical lead.
Figure 9B:
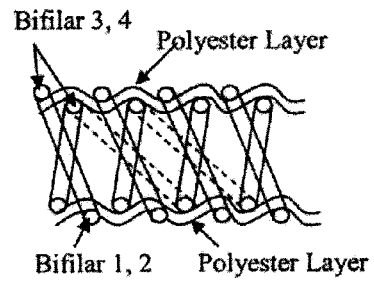
FIG. 9B is a longitudinal view of the electrical lead.

A first example of a transmission line lead is a multi-filar lead using various pitches and diameters. Note that a dual bifilar is discussed here, but other combinations are possible as well to increase the total number of conductors. The examples for the purpose of clarity will show a dual bifilar configuration. As shown in the schematic of FIG. 9A, this lead configuration has an air core to allow for a guide wire in one embodiment. A first conductor layer containing bifilar conductors 1 and 2 is separated from a second conductor layer containing bifilar conductors 3 and 4 by a suitable dielectric material (e.g., polyester). The second conductor layer is covered by an electrically insulating biocompatible material (e.g., urethane) to prevent external surface from coming in contact with body fluids (e.g., blood). A biocompatible material is a substance that is capable of being used in the human body without eliciting a rejection response from the surrounding body tissues, such as inflammation, infection, or an adverse immunological response. In one embodiment, the insulating material is applied around the layers of bifilar conductors as shown in FIG. 9B. The thickness of the insulating material is an important design consideration. In a preferred embodiment, the thickness of the insulating material is less than 0.5 mm. This design not only improves the structural integrity of the lead but also provides ample space for an air core for allowing insertion of a guide wire. However, care should be taken in this design to prevent any body fluid from entering at the ends of the lead. It should be noted that electrical properties of the lead are dependent on the inner insulation thickness as well as the permittivity of the insulating material. Further, it should be noted that the inductance of the lead increases with increased diameter of the helix of bifilar (or multi-filar) conductors. In practice, however, this diameter cannot be arbitrarily varied since it is fixed due to the restriction imposed on the dimensions of an intravascular lead structure. In any case, inner layer of conductors may be used for delivering stimulation in one embodiment while the outer layer of conductors may be used for transmitting back physiological parameters and other relevant data.

Figure 9C:
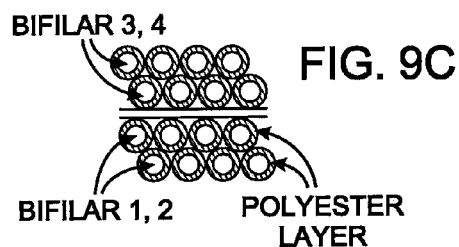
FIG. 9C is a longitudinal view of an alternative arrangement.

While this design differs from the traditional design of bifilar conductors shown in FIG. 9C in which each conductor has its own insulating material. This design requires more insulating material and is mechanically less robust. However, this design completely insulates the conducting wire from coming in contact with body fluids.

Figure 10:
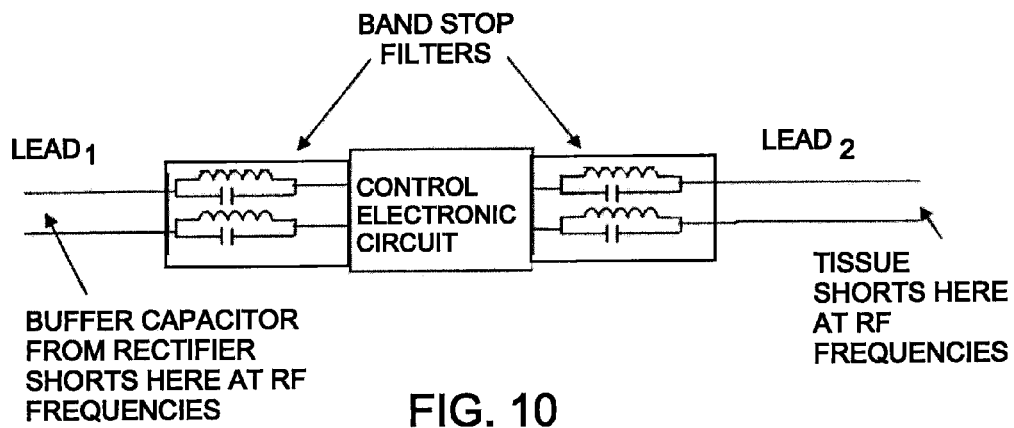
FIG. 10 is a schematic of the electrical lead and electronic circuit interface and lead and tissue interface.

In any case, the lead design should be such that at the RF frequency of interest it presents high impedance toward the electronic capsule and low impedance at the stimulating end of the lead. As shown in FIG. 10, the control electronic circuit module has bandstop (i.e., at the MR frequency) filters at the end connecting the control electronics circuitry. The length of lead1 and lead2 on opposite sides of the control electronic circuitry may be unequal in physical length but they need to be an odd multiple of quarter wavelength corresponding to 90, 270, 450 . . . degrees.

A second example of a transmission line lead may have a bifilar configuration. A bifilar clockwise, with coaxial bifilar counterclockwise lead can have controlled spacing between the coaxial layers wherein turns create inductance and the clock wise/counter clockwise layers will create a coaxial capacitor. The actual model is far more complex due to various coupling paths (inductive and capacitive). However, this design may provide a better level of control over the parameters of interest The transmission line's electrical length is tuned by building the lead from sections that are strung together to create L's, C's and R's using a two-step process. First, a conventional model is derived to determine locations and values of the resonant circuits along the lead. Second, components are created from lead topologies to create equivalent values. In an alternative method, one can create a plurality of physical models based on various parameters mentioned and measure the output to derive appropriate resonant circuit using well known statistical techniques. See a standard six sigma reference book for reference (*The Six Sigma Handbook* by Thomas Pyzdek, McGraw-Hill, 2000).

In a preferred embodiment of the present invention, RF energy deposition to the patient around a conductor is minimized by surrounding it with a physical layer that is neither a high conductor nor a high insulator. One aspect of the invention is to make a lead assembly in which one or more lead conductors individually or as a group have an RF energy dissipation and/or quenching layer made of a semiconducting material. While we describe the RF energy dissipation and/or quenching layer around a conductor, it should be understood that RF energy dissipation and/or quenching layer can be advantageously added to any metallic implant coming in contact with a patient's tissue. For example, in orthopedic implants, if highly conductive materials are needed, they can be coated with a layer of RF energy dissipation and/or quenching material. As another example, if conductive stents are needed they can be rendered MRI compatible using a layer of semiconducting material during the stent forming process. Such a semiconducting material may be formed using various methods described below.

Referring to FIG. 11A, the cross sectional view of the basic lead structure in the inventive subject matter has a single conductor 480 with an energy dissipation and/or quenching semiconducting layer 482. Additional biocompatible layer 484 may be formed as in a traditional implantable electrical lead. FIG. 11B is a longitudinal view of the lead assembly wherein the RF energy dissipation and/or quenching layer is formed around the central conductor.

In FIG. 12A an arrangement of multiple conducting wires (e.g., quad-filar) is described. In one embodiment, each conductor 500 may have a layer of RF energy dissipation and/or quenching electrically conductive material 510 and there can be a common biocompatible layer 520. In an alternative embodiment shown in FIG. 12B, multiple conductors 530 may have a common RF energy dissipation and/or quenching electrically conductive layer 535. Additionally, an additional biocompatible layer 540 is formed as in a traditional implantable electrical lead. The thickness of the layer may be adjusted based on the frequency of MRI application and may be based at least in part on the skin depth of the semiconducting material.

RF Energy Dissipation and/or Quenching Materials:

The choice of the RF energy dissipation material mainly depends on the purpose for the lead. It is also desirable that the RF energy dissipation material does not break off during chronic use and cause bio-hazard or other complications. In the following, a number of suitable candidate materials are described.

Carbon particles densely embedded in a polymer such as polyurethane may be used as an RF energy dissipation or quenching material. For this material to work, the carbon particles embedded in the polymer need to be touching each other to create a conductive layer. The density of the carbon particles may have to be adjusted to achieve the desired objective. Alternatively, graphite embedded in a rubber compound may be sprayed on to the conductors for a desired thickness. Alloys that have conductivity properties similar to that of graphite can be used as well. Semiconducting materials such as germanium can be used as a coated layer around the conductor. In general, the desired electrical conductivity for the RF energy dissipation material is in the range of $10^{-2}$ to $10^4$ Siemens per meter (S/m).

Instead of using semiconducting particles, carbon fibers can be woven into braids or knitted and used as an energy dissipation material. In a preferred embodiment, the carbon fibers may be closely braided with less than 20% open space in the braid. Braiding carbon is a well understood process and produced in industrial quantities by several companies including SPT Technology, Inc. of Minneapolis, Minn.

Another class of suitable materials is conducting polymers that have been a focus of attention among researchers for more than two decades, since the discovery of doped polyacetylene in the 1970's. Their relatively large conductivity, light weight and flexibility are just some of the factors that make conducting polymers much more desirable than metals in certain applications. Of the various conducting polymers studied, polyaniline (PANi) has been investigated the most due to its ease of synthesis, relatively high conductivity and good stability. Depending on the oxidation level, PANi can be synthesized in various insulating forms such as the fully reduced leucoemeraldine base (LEB), half-oxidized, emeraldine base (PANiEB) and fully-oxidized, pernigraniline base (PNB). Of these three forms, PANiEB is the most stable and widely investigated polymer in this family. PANiEB differs substantially from LEB and PNB in the sense that its conductivity can be tuned via doping from $10^{-10}$ up to 100 Siemens per cm and more whereas the LEB and PNB forms cannot be made conducting. Thus a doped PANiEB may be formed as a suitable RF energy dissipation material. See for example, Pure and Applied Chemistry Vol. 74, pages 857-867 (2002).

An Integrated Approach to MRI Compatibility

An integrated approach to MRI compatibility involves a lead assembly simultaneously satisfying the following conditions: (a) there are no susceptibility effects from materials used for the lead construction to avoid image artifacts; (b) the materials used are non-magnetizable to avoid image artifacts; (c) the lead design minimizes build up of induced common mode currents while the lead is being exposed to the MRI RF field; (d) the lead design minimizes pick up of the E fields from the gradient coil so that the lead structure is unaffected by the gradient field; (e) the lead is flexible enough to be usable for long term bio implant use, for example, in electrical stimulating devices such as cardiac pacemakers, defibrillators, and nerve stimulators; and (f) the lead is biocompatible such that it does not promote or cause any adverse reaction to the user. Thus, a key aspect of the invention is achieving simultaneous electrical, mechanical and biological compatibility.

The integrated approach enables conventional MRI imaging while reducing adverse effects to the patient or to the implanted device. One approach to achieving this goal is that the lead circuit is self-resonant wherein an inductance is formed in parallel with the lead's parasitic capacitance. The inductance is defined by the expression:

$$L'C=1/\omega^2 \quad (1)$$

where L' is the inductance per unit of length/of the lead, C is the parasitic capacitance per unit length, and ω is the Larmor frequency of the MRI scanner (e.g.; 64 MHz or 128 MHz), also referred to as the MRI resonant frequency. The lead's inductance and parasitic capacitance cause the lead to act as a parallel resonator, at the MRI resonant frequency. A parallel resonator has a high impedance across it. This impedance is Real at the MRI resonant frequency, and equal to $Q^2 \cdot R$, where Q is the quality of the resonance, and R is the series resistance in the parallel resonator.

In a conductor coil of length l, cross sectional area A, and m turns per unit length, the self inductance L is given by the equation (2) as described by B. I. Bleaney and B. Bleaney, Electricity and Magnetism, 2nd edition, Oxford University Press, 1965:

$$L=\mu\mu_0 m^2 Al \quad (2)$$

where μ is the magnetic permeability of air and $\mu_0$ is the magnetic permeability of a vacuum. For MRI compatibility of the lead, the length l of each conductor should not be a multiple of half a wavelength of the Larmor frequency of the tissue of the animal in which the lead will be implanted.

That means that if a coil is stretched, the inductance is decreases. The capacitance per unit of linear length between the wires also decreases as evidenced by the following equation:

$$C = \frac{\pi\varepsilon\varepsilon_0}{\log\left((d + \sqrt{d^2 - a^2})/a\right)} \quad (3)$$

or when d>>a: $C=\pi\varepsilon\varepsilon_0/\log(2d/a)$,
where d is half the distance between the centers of the adjacent wires, and "a" is the radius of the wire, see FIG. 13. When stretching a coil, both capacitance and the inductance reduce, but the capacitance reduces faster than the inductance in a region where the pitch of the windings is such that the windings are tightly packed (due to the log approaching zero). The self resonance frequency is inversely proportional to the square root of inductance times capacitance, so at some pitch of the conductor coil, the self resonance frequency crosses the Larmor frequency of the MRI system.

Achieving Electrical Compatibility:

The electrical compatibility is established by minimizing build up of the induction of the common mode current as described below: First approach involves a lead, for example, a transmission line type quad filar lead, forming a transmission line with an electrical length equal to ¼+N*½ wavelengths at the MRI RF frequency, while in the body as described earlier. At the RF frequency of the MRI system, the generator end should be terminated. The lead can be constructed to provide local parallel resonance presenting very high impedance at the resonant frequency inhibiting current patterns to be established on the lead when exposed to an excitation field. This method is useful for a higher MRI field strength, such as 3.0 T, where the image quality aspects of the lead are a bigger challenge as compared to 1.5 T or lower. A second approach involves placing RF blocking networks in the lead at least quarter wavelength locations as described earlier. Note that for 3.0 T the wavelength is half that of the 1.5 T field strength. Thus, to address the issue for these two field strengths, the networks would be placed at greater or equal to the quarter wavelength of the highest frequency (approximately 128 MHz) encountered. For the lower 1.5 T frequency there would thus be redundant networks as they would appear at every ⅛ wavelength. However, this redundancy does not adversely affect the blocking function. A third approach involves using a combination of the first and the second approaches. A fourth approach involves reducing the ability of the lead to be an antenna, i.e., a receptacle for RF energy. If the lead could be presented to the surrounding field as a low quality antenna, the amount of energy absorbed would be reduced. This quality reduction can be accomplished by adding damping to the lead, or a way to dissipate the absorbed energy in such a way that no focal spots in the E field or high voltage points will exist. Since focal spots in the E-field can be created by concentration of E-field, such as at tips or ends of wires or components, any sharp edge or point is avoided. For non-sharp objects such as lead conductors, further energy damping can be provided by coating the lead conductor with a medium grade conductor to provide sufficient resistivity to dissipate energy.

Unlike prior art methods of using a shield around the lead, which will make the shield itself carry the standing wave induced by the transmit pulse, our inventive approach uses the following key points: First, our approach makes the lead itself to be a high impedance structure at the Larmor frequency of the MRI system, e.g. by making the lead in the form of a choke, or by putting in discrete band stop filters. Second, the inventive approach uses a layer around the lead that absorbs the energy associated with any remnants of the induced standing wave. The current approach is quite different from the methods that conduct energy of the standing wave to the surrounding tissue. This approach is further described with the following three configurations.

Prevention of Lead Becoming an Antenna

Figure 13:
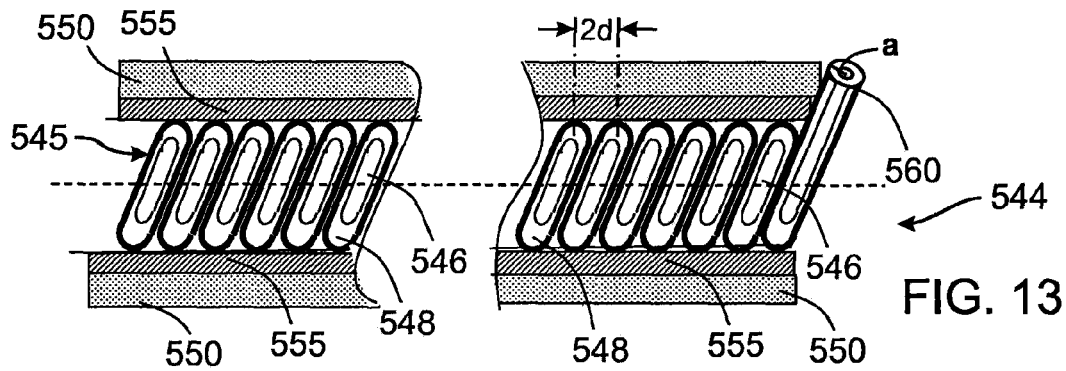
FIG. 13 is a schematic longitudinal view through a lead assembly with a single layer, multiple coil configuration.

Single Layer, Multi-Wire Lead Configuration:

Referring to FIG. 13, a single layer, multi-wire lead 544 comprises of single coil 545 comprising a conductor 546 covered by insulation 548 forming the central structure. The insulated, coiled conducting wires are coated by a tubular damping layer 555 of medium conductive material mentioned before. That entire structure is covered by a biologically compatible electrical insulating layer 550. The distal part of the lead, that is less than one eighth of the wavelength, need not be coated with a medium conductive damping layer 555. The conductive damping layer 555 plays a role in dissipating some of the energy from the MRI fields evenly into the surrounding animal tissue over the entire length of the lead, such that there are no hot spots. Because the outer biocompatible layer 570 serves as a capacitance to the surrounding tissue, that layer should be as thin as possible to maximize that energy dissipation.

The multiple conductive wires in the lead usually terminate in an electrode (not shown) that is in contact with the tissue to be stimulated. One such terminus 560 is shown in the FIG. 13. Note that if there are multiple coils, each of them will have a terminus similar to 560. Further, note that in this configuration, all the coiled conductors are in one layer. Different variations of this fundamental lead configuration provide the following multiple implementations.

A first implementation may include: a) a single or multifilar (e.g., 1, 2, 3, 4, . . . n conductors) helix, with individually insulated conductors having a specific pitch (turns per unit length) to form a parallel resonant circuit with the inherent inter winding structural capacitance and the inherent lead inductance; b) a damping layer made from a medium conductive coating, such as a conductive polymer, carbon containing or other conductive material in order to render the layer conductive, but to a particular conductivity (1.0 to $2 \times 10^5$ Siemens per meter); c) an insulating layer with a specific dielectric constant to work in conjunction with helical layer described in 'a' and the damping layer described in 'b'; d) biocompatible layer covering 'b' from which no connection to the outside of the lead surface is made; and e) an additional single or multi filar helix with counter wound conductors as described in detail later in the specification.

In a second implementation, the structure is similar to the first implementation except that the damping layer is applied in segments, with or without any bridging elements.

A third implementation has a structure similar to the first implementation except that the pitch of the coiled conductor 546 varies along the lead length to provide a different tuning (i.e. resonance) depending on position along the lead. A short section (e.g. the last 25%) of the lead can be modified this way. For example, different conductor pitches can be used near the signal generator (e.g., pacing device) as in contrast to the stimulation site (e.g., heart). This choice depends on a trade-off between desired mechanical flexibility and degree of lead damping required. Mechanical flexibility is generally higher if the pitch is lower. RF damping of the lead, on the other hand, is higher with larger pitch. There are other effects that need consideration while increasing the pitch. One effect involves the lowering of the self-resonance of the effective LC circuit formed by the lead with larger pitch due to the inverse relationship between the LC-product and square of the self-resonance frequency. Another effect involves the length of the MRI RF body coil and the type of RF body coil. This affects the E field amplitude during the MRI RF pulse, but the frequency to be blocked is still the same. Therefore, changing the lead pitch also causes the MRI frequency that will be blocked to change.

A fourth implementation includes combination of the previous three implementations to obtain additional degrees of tuning depending on the application. Since MRI compatibility, site stimulation, data sensing, lead longevity and mechanical flexibility are all requirements that must be simultaneously met, a combination approach may provide optimal lead configuration in the implementation of an MRI safe lead.

Figure 14:
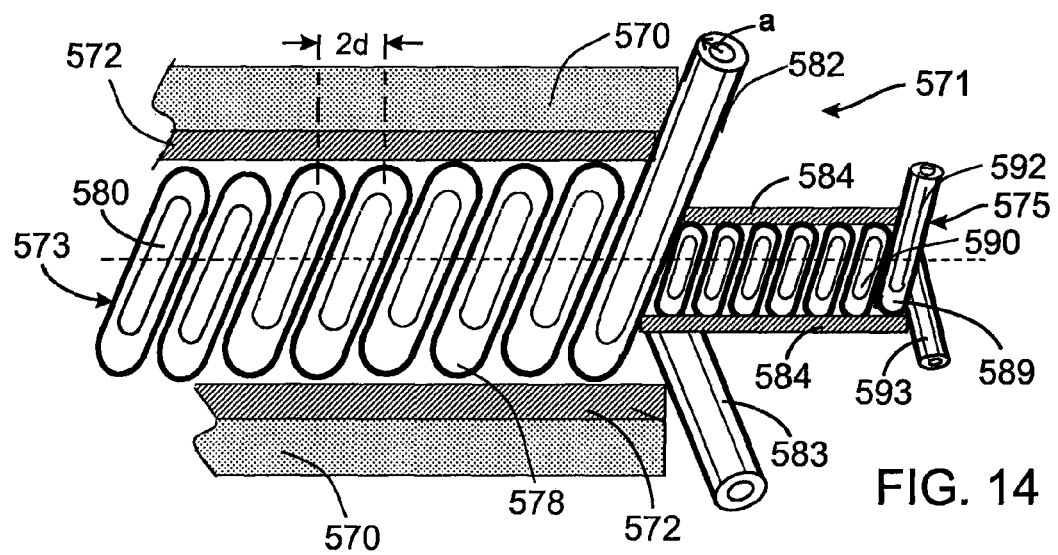
FIG. 14 is a schematic longitudinal view through a lead assembly with a multi-layer, multiple coil configuration and separate conductive layers for each coil.

Multi-Layer, Multi-Wire Lead Configuration:

With reference to FIG. 14, the lead 571 has two coils 573 and 575 that form outer and inner layers of conductors 580 and 590, respectively, each conductor layer of the type previously described for the single layer configuration. An example of this type could be a bifilar configuration in which there are two coiled conductive wires with each layer. The outer and inner conductor layers are separated by a spacer layer 584 of an dielectric material. In the above-mentioned bifilar configuration, two termini 582 and 583 from the outer layer and two termini 592 and 593 from the inner layer are available for connecting to the electrode elements (not shown). It should be noted that the multi-layer, multi-wire lead configuration can approximate a single layer, multi-wire configuration described previously if the spacing between the inner and outer layers of conductors 580 and 590 is less than an empirically determined thickness. For example, in one embodiment, if the spacing is less than 0.5 mm, a virtual single layer, multi-wire configuration is achieved. It should be further noted that the spacing might be due to an insulating material of a particular design choice. Those insulating materials are previously described.

The illustrated two layer, multi-wire lead 571 comprises of multiple coiled outer conductors such as 580 covered by insulation 578 and also comprises multiple coiled inner conductors such as 590 covered by insulation 589. Combined the coiled inner and outer conductors form a central structure of the lead. The insulated, coiled outer coil 573 is coated by a surrounding layer 572 of a medium conductive material as mentioned before, which layer covered by a biologically compatible and electrically insulating layer 570. The distal part of the lead, that is less than one-eighth of the wavelength of the MRI signal, need not be coated with the conductive layer 572. Each conductive wire in the outer layer of conductors 580 has a terminus 582 or 583 at which an electrode (not shown) usually is located to contact the tissue to be stimulated. Similarly each conductive wire in the inner layer of conductors 590 has a terminus 592 or 593.

Alternatively, the spacer layer 584 may be formed of a medium conductive material having a conductivity in the range 1.0 S/m and $2\times10^5$ S/m, either in addition to or in lieu of the outer conductive layer 572 that surrounds both the outer and inner layers of conductors 580 and 590, respectively.

Figure 15:
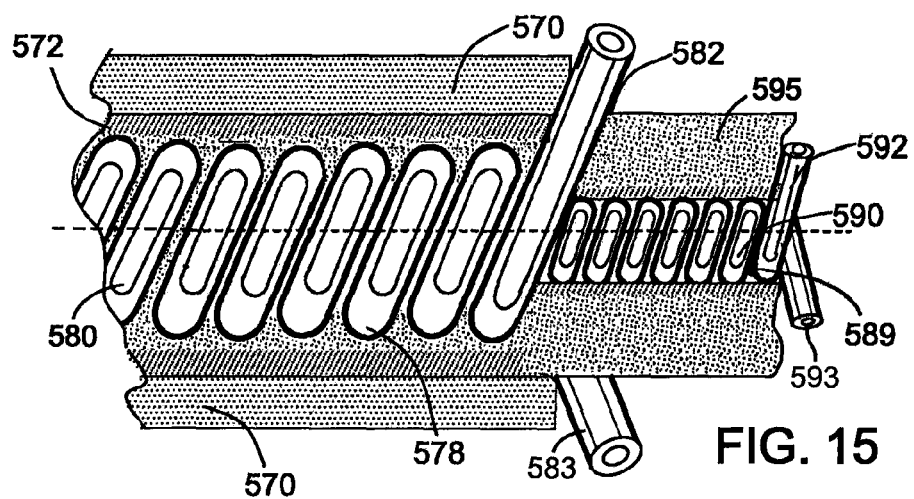
FIG. 15 is a schematic longitudinal view through a lead assembly with a multi-layer, dual coil configuration in which an outer coil is encased in an electrically conductive layer.

With reference to FIG. 15, both the outer and inner layers of conductors 580 and 590 alternatively are embedded in a common layer 595 of a medium conductive material having a conductivity in the range 1.0 S/m and $2\times10^5$ S/m. In particular the outer layer of conductors is encased in the layer 595 of conductive material.

Figure 16A:
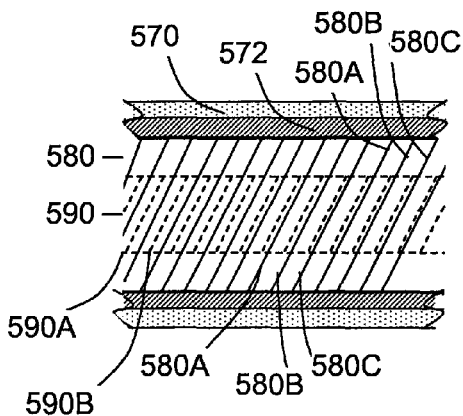
FIGS. 16A and 16B schematically show longitudinal views of two alternative ways of winding conductors in a lead assembly with a multi-layer, multiple coil configuration.
Figure 16B:
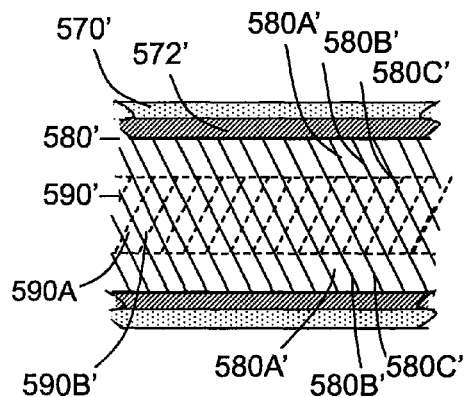

FIGS. 16A and 16B further illustrate alternative arrangements possible with variations in winding directions in a bi-layer, bifilar example. In this example, it should be noted that both inner and outer layers have multiple insulated conductors wound on each layer. The number of insulated conductors for these two layers may be the same or they may be different. In one embodiment, FIG. 16A shows three insulated conductors 580A, 580B and 580C are wound on the outer layer and two insulated conductors 590A and 590B are wound on the inner layer. An optional spacer layer (not shown) may be present between inner and outer layers. The winding directions of insulated outer conductors 580 may be in the same direction of the insulated inner conductors 590 as shown in FIG. 16A or they may be in different direction as shown in FIG. 16B. In some embodiments, the conductive layer 572 and the biocompatible external layer 570 may be separate layers as shown in FIG. 16A. In an alternative embodiment, these layers may be combined into one layer. This would be the case when the medium conductive material also happens to be biologically compatible. In any event, the external layer is in contact with a body tissue or body fluids.

Figure 17A:
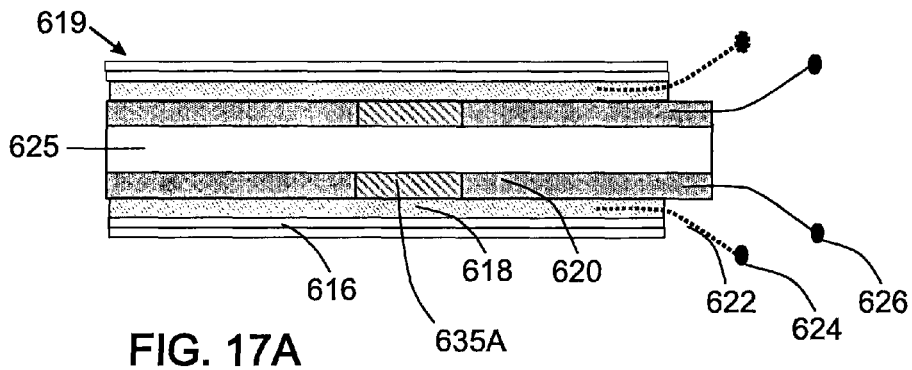
FIGS. 17A and 17B schematically illustrate longitudinal views of the lead assembly with a multi-layer, multiple coil configuration in compressed and extended states, respectively.
Figure 17B:
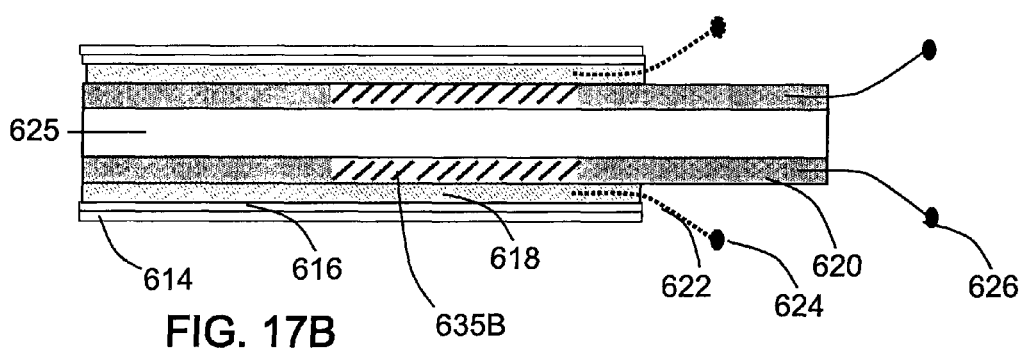

Multi-Layer, Multi-Wire Lead Configuration with Adjustable Electrode Distance:

Now referring to FIGS. 17A and 17B, we illustrate a special type of lead 619 which is similar to the previous multi-layer, multi-wire lead configuration of FIGS. 14 and 16 but with a key difference. The inside layer is designed to be adjustable so that the distances between electrodes 624 and 626 connected to the coiled wire termini can be adjusted during the implantation. Thus the extendable lead allows for deployment of electrodes at locations with variable distance as shown by the extension of original space 635A in FIG. 17A to extended space 635B in FIG. 17B. The lead is composed of an outer layer 618 and inner layer of conductors 620, each having one or more coiled insulated conductors. The inner layer contains a section which can be extended or contracted by means of an inner guide wire or sheath (not shown) that can be brought in through the central space 625. Since locations of stimulation or sensing in an organ, for example, heart, is not accurately predictable and varies amongst individuals, usually multiple leads are inserted to reach two locations for sensing and or stimulation. This configuration allows a single lead to fulfill this need, obviating the need for multiple leads and simplifying the procedure. When the inner lead is extended, it does change the overall length of the lead structure, but without changing the length at the other, non-extendable end. In one embodiment shown in FIGS. 17A and 17B, when the extension range is less than 7.6 cm, one may not use the extra layers of medium conducting material and the metal patches at quarter wavelength intervals on the extended part of the lead. In this embodiment, a medium conducting layer and a biocompatible insulating layer are also added over the conductors on the extended part.

Referring to FIG. 17, an adjustable two layer, multi-wire lead 619 comprises of multiple coiled outer layer of conductors 618 covered by insulation and inner layer of conductors 620 covered by insulation forming the central structure. The insulated, coiled outer conducting wires are coated by a layer 616 of medium conductive material mentioned before, which layer is biologically compatible and electrically insulating. The distal part of the lead less than one eighth of the wavelength need not be coated with a medium conductive layer 616. The conductive wires in the lead 619 usually terminate at a bare, non-insulated terminus 622 and an electrode 624 or 626 that are in contact with the tissue to be stimulated. The terminus 622 is a bare, non-insulated portion of a conductor in the outer layer of conductors 618, which is adapted to be exposed to body tissue or body fluids upon implantation in an animal. The length of the terminus 622 is determined by a wavelength which is a function of the velocity (v) of the electromagnetic wave in the animal tissue divided by the frequency of the electromagnetic wave. The velocity is the inverse of the square root of the product of permittivity and permeability of the tissue. Therefore the terminus length (TL) is defined by the expression TL<(¼) (v/f), where (f) is the Larmor frequency of a magnetic resonance imaging scanner. In an exemplary embodiment where there are two coils in the inner conductive wires and two coils in the outer conductive wires, each of those conductive wires has a separate terminus and electrode.

In the configurations described above, the coil turns per unit distance, coil structure diameters, distance between inner and outer insulated conductors, conductivity of a layer of medium conducting material, dielectric medium between the conductors as characterized by relative permittivity of the dielectric, and total length of the lead are adjustable parameters that can be chosen based on the field strength of the MRI scanner. The winding directions of insulated outer conductors may be in the same direction of the insulated inner conductors or they may be in different direction. Additionally, the transmission line characteristic impedance (CI) is also an important design parameter. This is the virtual impedance of any wire pair. For example, television coaxial cables have a typical characteristic impedance of 50, 60 or 75 Ohm; for phone lines, the CI is 600 Ohm; and for ribbon cable with 1.3 mm pitch, CI is 110 Ohm. In the present case, there may be two transmission lines, inner and outer, each with their own CI in the range of 10 to 1000 Ohm.

The above parameters have the following preferred ranges of values: turns per unit length may be same or different for the inner and outer layer of conductors with a range of 4 turns per centimeter to 40 turns per centimeter; conducting wire diameter: 0.05 mm to 0.25 mm; inner coil diameter: 0.635 mm to 1.524 mm; outer coil diameter: 0.76 mm to 2.54 mm; dielectric thickness: 0.01 mm to 0.20 mm; relative permittivity of dielectric: 1 to 15; conductivity of the medium conductive layer: 1.0 S/m and $2\times10^5$ S/m; and the total length of the lead is chosen based on the physiological requirement and MRI field strength.

MRI Compatible Defibrillation Lead:

For an MRI compatible defibrillation (ICD) lead, the lead coil section that forms one of the contacts, is not modified for MRI compatibility. It does not contain any materials that have a magnetic moment, such as soft iron, nickel or cobalt, as their presence would cause image artifacts. If the unmodified section is less than any quarter wavelength (in body fluid) of the MRI scanner, there will not be any image quality (IQ) issues. In general the IQ issues increase with field strength, with most issues anticipated at the common 1.5 T and 3.0 T field strengths. In these cases, a 5 cm to 7 cm segment may be left partially unmodified, without causing significant adverse IQ affects. It should be noted that a pacing lead can also be left unmodified over the last 5 cm to 7 cm segment without causing adverse MR IQ effects in 1.5 T or 3.0 T imagers.

Figure 18A:
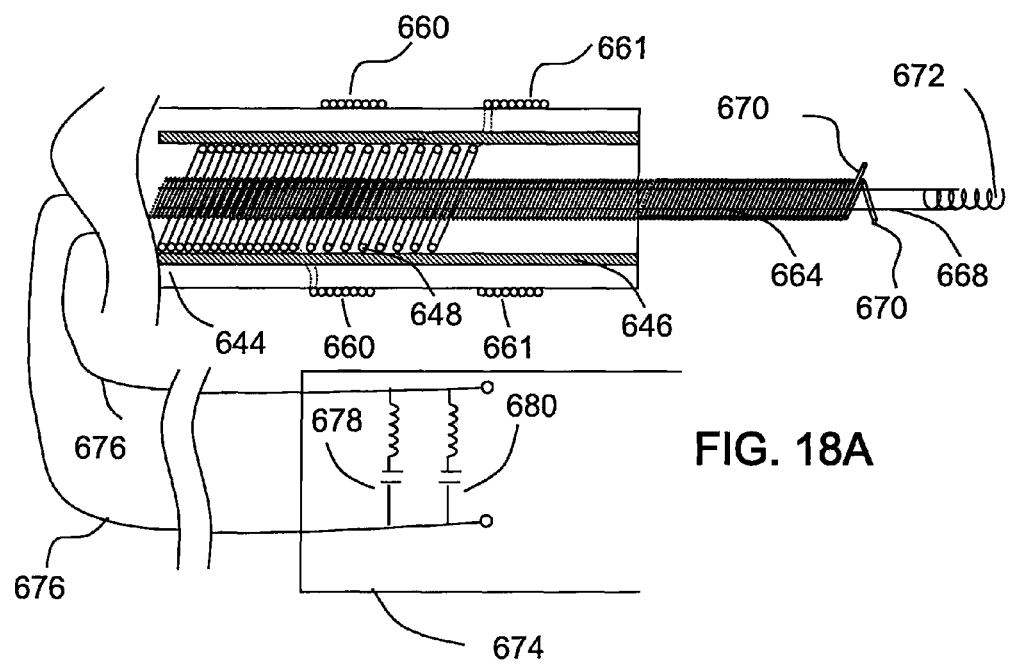
FIG. 18A is a schematic of the MRI compatible defibrillation lead with series resonant circuits across the lead.

Referring to FIG. 18A, a defibrillation lead comprises of multiple coiled conductors such as 648 covered by insulation forming the central structure. The insulated, coiled conducting wires 648 are coated by a layer 646 of medium conductive material mentioned before. The entire structure is covered by a biologically compatible insulating layer 644. In an exemplary case of two electrode defibrillator, the insulated conductor comes out of the lead body without insulation and is wound on the lead body without touching each winding of the coil as electrodes 660 and 661.

The proximal end of the insulated conductors 676 are connected to a series resonant circuits 678 and 680 which are tuned to short out the defibrillator circuit at the resonant frequencies of 1.5 T scanner (64 MHz) and 3.0 T scanner (128 MHz) respectively. Similar series resonant circuits may be provided for other scanners as well. The resonant circuits are housed in the ICD container 674.

Figure 18B:
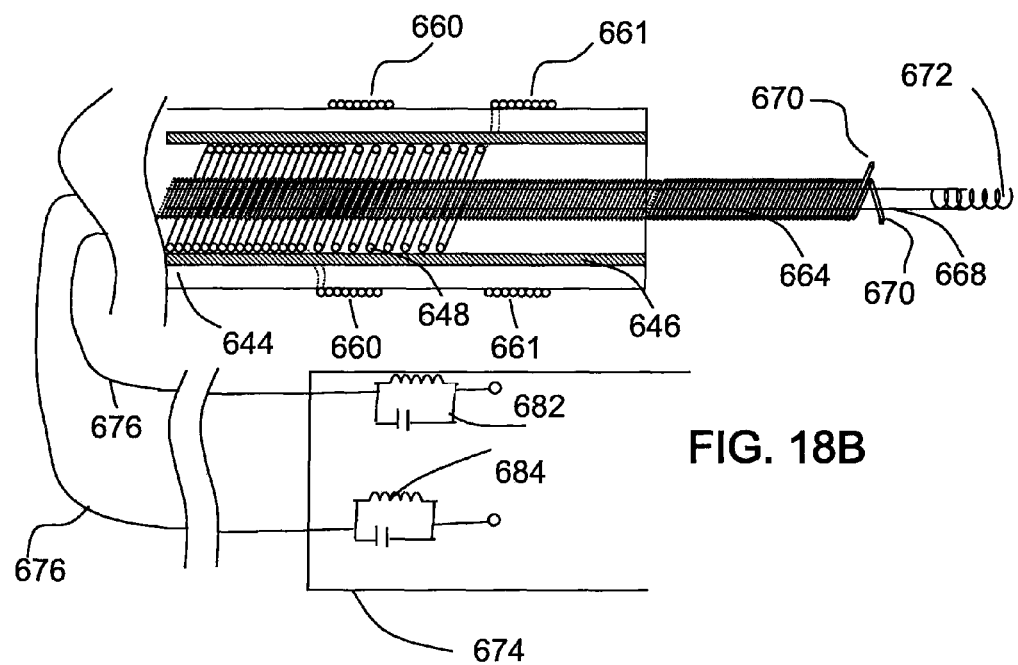
FIG. 18B is a schematic of the MRI compatible defibrillation lead with parallel resonant circuits along the lead.

Alternatively, as shown in FIG. 18B, the proximal end of the insulated conductors are connected in series to parallel resonant circuits 682 and 684 which are used for blocking any MRI induced current. The resonant circuits are housed in the ICD container 674.

Additionally, the inner coiled insulated conductor 664 is for cardiac pacing. The end termini 670 are connected to the pacing electrodes (not shown). If the inner insulated conductor for pacing is more than one-eighth of a wavelength of the MRI scanner in contact with the body fluid or tissue for pacing, then the medium conducting coating covers the surface of the inner conductor 664 followed by an outer insulating layer. The inside tube 668 is present through out the lead and is terminated with an anchoring component 672 which helps in the anchoring of the lead. The anchoring component is made up of an MRI compatible material described earlier. The winding directions of insulated outer conductors may be in the same direction of the insulated inner conductors or they may be in different direction.

Achieving Mechanical and Biological Compatibility:

The mechanical and biological compatibility is obtained using the steps described below: First, the flexibility of the lead is required to allow for the lead to follow the body and intra-organic movements, without impediment. Second, the fatigue resistance is essential for many applications, for example, in a cardiac apex application, the lead end would flex with each heart beat. Third, considerations are given to satisfy both flexibility and fatigue resistance simultaneously in addition to providing biocompatibility. Polyurethane materials are used for the lead body to meet all the three criteria. In addition, the conductor material is chosen from the well known alloys, for example MP35 alloy or stainless steel, which are specifically designed to have a very high fatigue resistance and tensile strength against breakage. In general, a biologically compatible material does not adversely affect the surrounding tissue of an animal in which the material is implanted.

Referring to FIGS. 4 and 7, the housing 42 of the implantable medical device 40 also has been uniquely constructed to be compatible with an MRI scanner. FIG. 7 shows a cross section through one exterior walls 66 of that housing 42. The wall is electrically conductive to shield the internal electronic circuitry from radio frequency interference during normal operation. Specifically, the housing walls are conductive at RF frequencies, but have high impedance at the frequency associated with the leading and trailing edges of the MRI gradient pulses, thus preventing gradient eddy currents in the walls. The exemplary wall 66 is formed by outer conducting layers 52 and 54 of aluminum, copper, or other electrically conductive, non-ferromagnetic material applied to the major surfaces of a substrate 56 of dielectric material, thereby forming a laminated wall with the substrate sandwiched between two conductive layers. The first layer 52 is on the exterior surface 51 of the substrate 56, and the conducting second layer 54 is on the interior surface 53 of the substrate.

A plurality of slots 58 and 60 are made through the first and second layers 52 and 54, respectively, to expose dielectric substrate 56, thus creating a plurality of conductive segments 62 and 64 which form stripes on the opposing surfaces of the substrate 56. The first slots 58 in the first layer 52 are offset in the plane of the wall from the second slots 60 in the second layer 54 so that there is not a direct electrical path through both layers 52 and 54. RF continuity is ensured via the capacitance coupling created through the dielectric substrate 56 between opposing conductive segments 62 and 64. The spacing between the slots on each dielectric surface is a function of the slew rate or rise time of the MRI gradient signal. Shorter rise times of the gradient pulses require smaller metallic surfaces to keep gradient eddy currents to an acceptable predefined level which will not adversely affect the animal. For example, a typical MRI gradient signal pulse requires each conductive segment 62 and 64 to be ten square centimeters or less.

With respect to FIG. 4, note that the slots 58 in one wall 66 of the housing 42 are not aligned with nor parallel to the slots 58 in an adjacent abutting wall 67 or 68. The same is true for the hidden walls in the drawings. A slot 58 also extends along each corner of the housing where two walls meet, so that the conductive segments 62 in the walls are not electrically connected. The same misalignment exists on the interior surfaces of the walls.

FIG. 8 illustrates an alternative arrangement of the slots in the exterior surface 51 of the housing 42. A first group of slots 80 extend transversely, preferably orthogonally, to a second group of slots 82, thereby forming a two dimensional array of conductive segments 84 in the electrically conductive first layer 86. A similar arrangement of transverse groups of slots form another two dimensional array of conductive segments on the second layer that forms the interior surface of the wall. The exterior and interior arrays are offset in both directions to overlap thereby capacitively coupling the first and second layers.

Implantable Enclosure with an Antenna Module:

An antenna module makes use of an alternative EMI prevention method involving an inductive antenna and a non-conductive enclosure. These changes permit the power and/or communication antenna to be placed inside the enclosure or be integrated in the enclosure itself. These novel modifications are described in further detail below.

Figure 19:
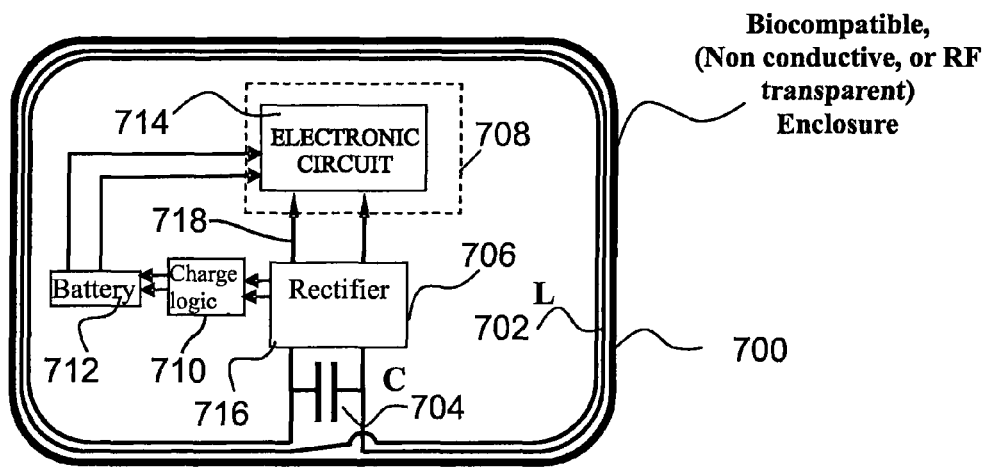
FIG. 19 is the schematic of an MRI compatible power antenna and associated shielded electronic circuitry inside an RF transparent enclosure.

Power Antenna:

As shown in FIG. 19, a magnetic field power antenna module comprises of an inductor element 702, which is looped around inside an enclosure casing 700. Alternatively, a coil pattern may be formed inside the enclosure to serve a similar purpose. The inductor L forms an inductive pickup loop and the two ends of this loop are connected to a capacitor 704. L and C form a resonant tank circuit, allowing for maximum energy transfer at the frequency $F=1/(2\pi\sqrt{LC}$. This power antenna is well suited for highly efficient, resonant transfer of energy. The energy is converted to DC by the rectifier 706 and is used by the electronic circuit 714 for providing therapy and or data acquisition. The enclosure casing 700 is biocompatible, non-conductive and radio frequency transparent.

The electronic circuit 714 is enclosed by an electromagnetic shield 708 which is similar to the housing 42 described in detail with reference to FIG. 7. Alternatively, it may be connected to a ground plane. For the EMI shielding of the enclosure or the electronics, a mesh may be used. In the MRI scanner, phosphor bronze and stainless steel meshes with a wire density of 128 lines per centimeter may be used in an exemplary case. These meshes have good conductivity at radio frequencies, but have high impedance at the MRI gradient frequency.

The power induced by external power supply (not shown) to the antenna mentioned above may be bypassed by a command to the charge logic 710. In that case, the shielded internal electronics circuit is powered by an internal battery 712, which may be a traditional battery or a rechargeable battery that is recharged via energy efficient, resonant inductive coupling mentioned before.

Figure 20:
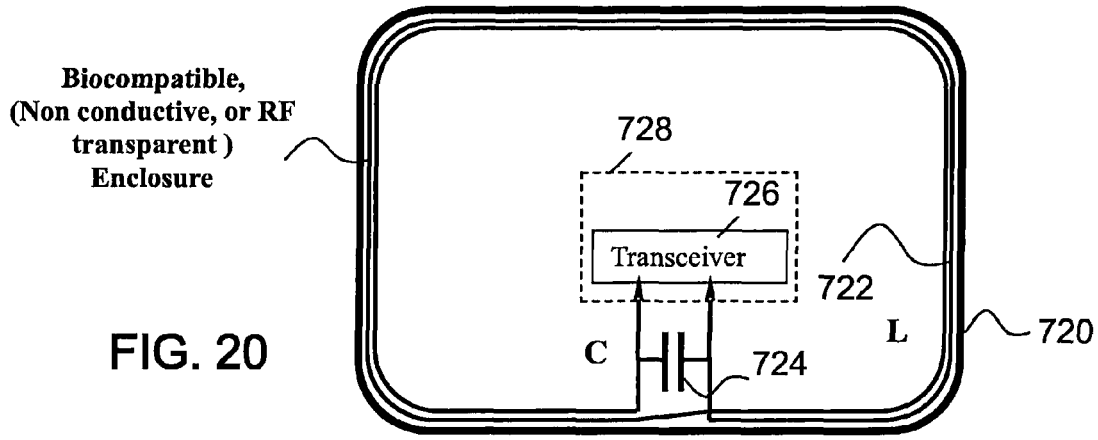
FIG. 20 is the schematic of an MRI compatible communication antenna and associated shielded transceiver circuitry inside an RF transparent enclosure.

Communication Antenna:

As shown in FIG. 20, a communication antenna module is formed inside an enclosure casing 720, with loops of inductive wire L 722 forming a pickup loop. Alternatively, a coil pattern may be formed inside the enclosure to serve a similar purpose. The ends of the loop are connected to the capacitor C 724. Elements L and C form a resonant tank circuit, allowing for maximum energy transfer at the frequency $F=1/(2\pi\sqrt{LC}$. The tank circuit may be a part of the data communication and reception that is performed by a transceiver 726. The enclosure casing 720 is biocompatible, non-conductive and radio frequency transparent. The transceiver 726 may be enclosed by an electromagnetic shield 728 which is similar to the housing 42 described in detail with reference to FIG. 7. Alternatively, it may be connected to a ground plane. For the EMI shielding of the case or the electronics, a mesh may be used. In the MRI scanner phosphor bronze and stainless steel meshes with a wire density of 128 lines per centimeter may be used in an exemplary case. These meshes have good conductivity at radio frequencies, but have high impedance at the MRI gradient frequency.

Blocking RF Voltage Entering Canister:

Usually a canister houses the electronics module that may comprise of stimulation signal generator and control electronics. In order to protect the electronics module, the RF voltage entering should be blocked. There are two cases that need to be considered while blocking the RF signals entering the canister. In the first case, the canister is one of the electrodes and therefore, it is electrically conducting. In the second case, the canister is not electrically conducting. The RF blocking for these two cases is described next.

Figure 21:
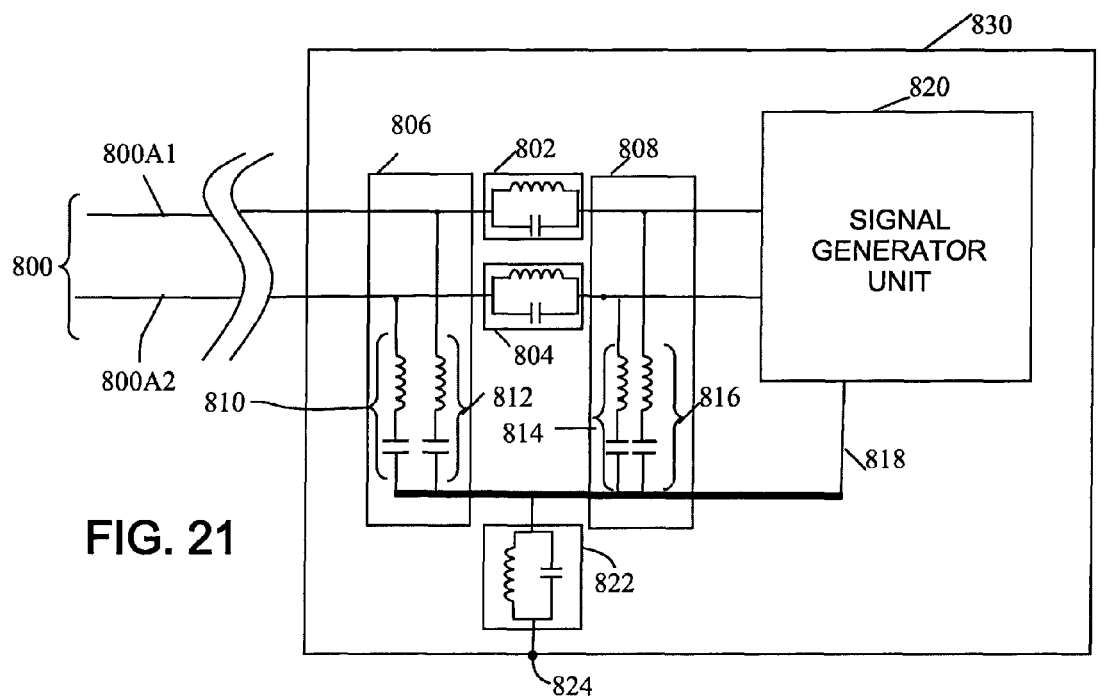
FIG. 21 is the schematic of RF blocking network in the case of a conductive canister.

RF Blocking in the Case of a Conducting Canister:

Referring to FIG. 21, the most generic case of RF blocking for a conducting canister is described. There are one or more leads 800 entering the canister 830, which houses the control electronics and the signal generator unit 820. For the sake of simplicity for illustrative purposes, only two leads 800A1 and 800A2 are shown in the FIG. 21. In any case, each lead is connected to a parallel tank circuit before it is connected to the signal generator unit 820. The parallel tank circuit acts as a band stop filter at the MRI frequencies. For example, parallel tank circuit 802 blocks the RF from the lead 800A1 at 64 MHz or 128 MHz. Similarly, parallel tank circuit 804 blocks the RF from the lead 800A2 at 64 MHz or 128 MHz. Each lead is also connected to an RF shunt module 806 located before the parallel tank circuit and having two RF shunt branches 810 and 812. Additionally, an RF shunt module 808 with two RF shunt branches 814 and 816 can be after the parallel tank circuit. The RF shunt branches 810-816 operate at MRI RF frequencies (e.g., 64 MHz or 128 MHz) and short those frequencies in order to prevent them from entering the signal generator unit 820. The other end which is away from the lead is connected to the electronic module common bus 818. In this embodiment, prior to connecting to the canister at node 824, the common bus 818 is connected to a parallel tank circuit 822 to block RF and pass other waveforms to the canister.

Having described the most generic embodiment, it should now be noted that many of the components can be taken out for specific embodiments. In one embodiment, module 806 may be taken out. In another alternative embodiment, module 808 may be taken out. In another alternative embodiment, both modules 806 and 808 may be taken out. In yet another embodiment, parallel tank circuits acting as band stop filters may be taken out while retaining the one or more of RF shunt modules. In this embodiment, the lead would be directly connected to the electronics module. In yet another embodiment, the bandstop filter 822 connecting the electronic module's common bus 818 to the canister may be taken out so that the common bus is directly connected to the canister 830.

Figure 22:
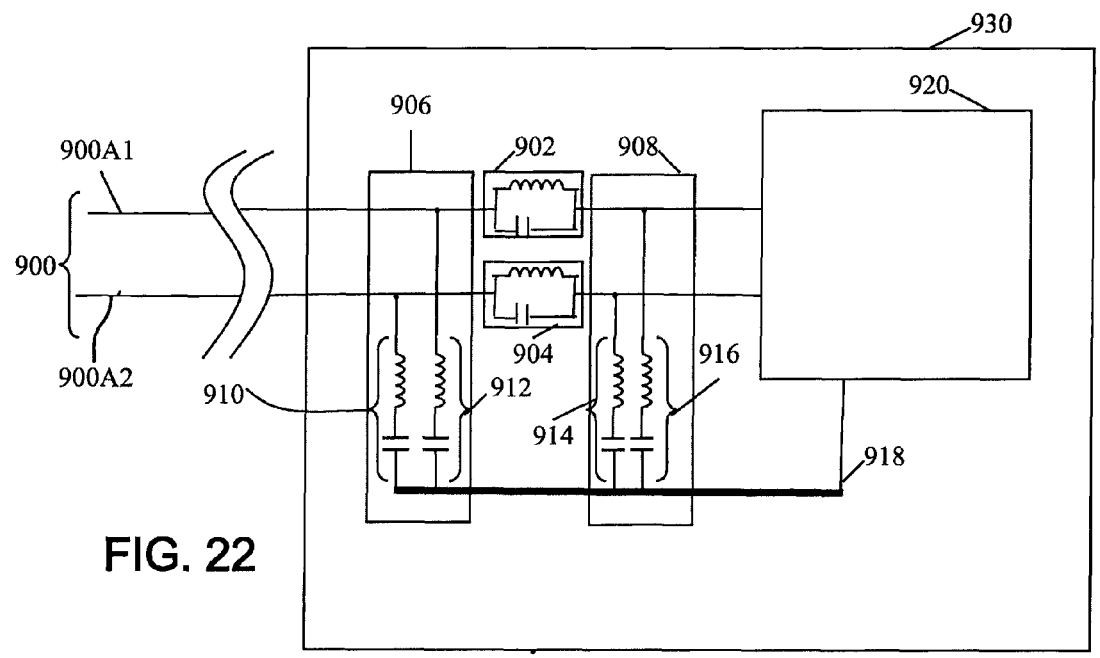
FIG. 22 is the schematic of RF blocking network in the case of a non-conductive canister.

RF Blocking in the Case of a Non-Conducting Canister:

Referring to FIG. 22, the most generic case of RF blocking for a non-conductive canister is described. There are one or more leads 900 entering the canister 930, which houses the control electronics and the signal generator unit 920. For the sake of simplicity for illustrative purposes, only two leads 900A1 and 900A2 are shown in the FIG. 22. In any case, each lead is connected to a parallel tank circuit before it is connected to the signal generator unit 920. The parallel tank circuit acts as a band stop filter at the MRI frequencies. For example, parallel tank circuit 902 blocks the RF from the lead 900A1 at 64 MHz or 128 MHz. Similarly, parallel tank circuit 904 blocks the RF from the lead 900A2 at 64 MHz or 128 MHz. Each lead is also connected to an RF shunt module 906 located before the parallel tank circuit and having two RF shunt branches 910 and 912. Additionally, an RF shunt module 808 with two RF shunt branches 814 and 816 can be after the parallel tank circuit. The RF shunt branches 910-916 operate at MRI RF frequencies (e.g., 64 MHz or 128 MHz) shorting these frequencies in order to prevent them from entering the signal generator unit 920. The other end which is away from the lead is connected to the common bus 918 which in this embodiment is not connected to the canister 930.

Having described the most generic embodiment, it should now be noted that many of the components can be taken out for specific embodiments. In one embodiment, module 906 may be taken out. In another alternative embodiment, module 908 may be taken out. In another alternative embodiment, both modules 906 and 908 may be taken out. In yet another embodiment, parallel tank circuits acting as band stop filters may be taken out while retaining the one or more of RF shunt modules. In this embodiment, the lead would be directly connected to the electronics module.

Blocking Gradient Voltage Entering the Canister:

Gradient generation in an MRI scanner can potentially induce large amplitude, slow varying voltage in the electronic circuitry inside the canister. Although such induced voltage may not cause any damage at a casual glance, it has a potential to cause cumulative damage to circuitry over a long period of time causing the implanted electronics to fail or mal-function prematurely. Therefore, measures need to be taken to block gradient generation induced energy affecting the canister.

Figure 23:
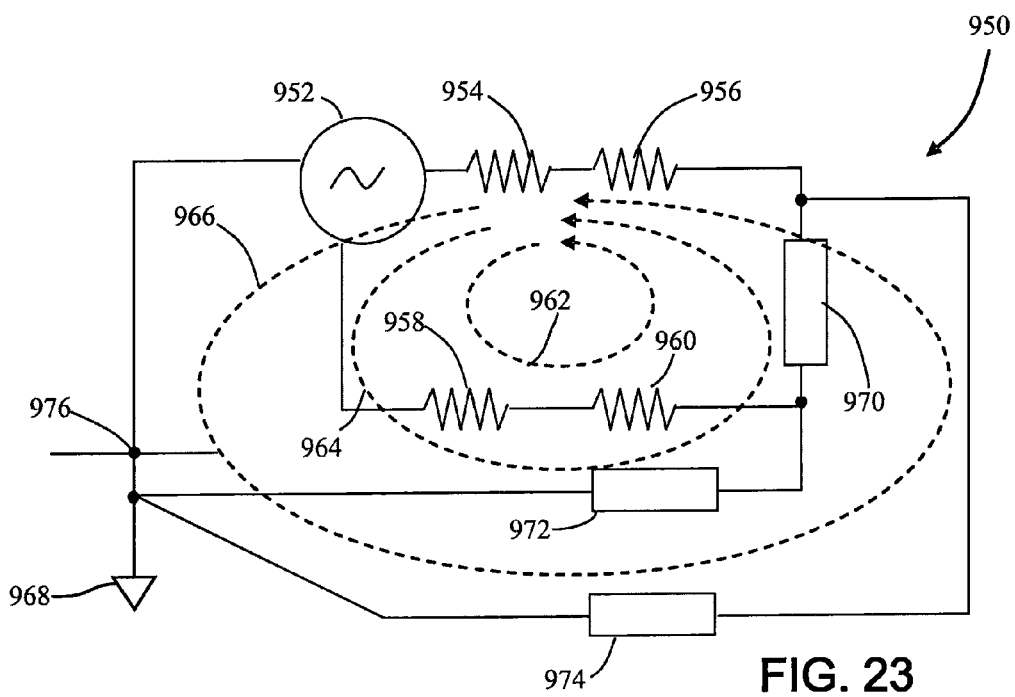
FIG. 23 is the schematic of gradient induced voltage loops in a conventional grounded stimulation system.
Figure 24:
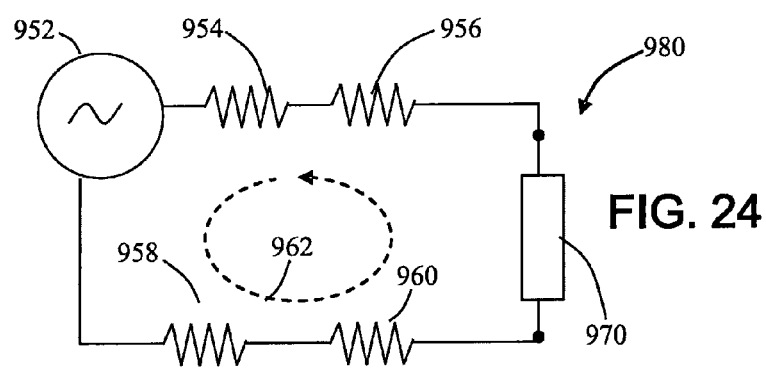
FIG. 24 is the schematic of gradient induced voltage loop in a stimulation system with internal reference.

A schematic of gradient induced voltage loops in a conventional implanted device 950 is shown in FIG. 23. The gradient pickup loops 962, 964 and 966 are formed when the canister ground 976 is connected to the implant body ground 968. The gradient voltage generator 952 effectively drives the current through the lead1 elements 954 and 956, lead2 elements 958 and 960, tissue impedance at the stimulation site 970, ground loop to the lead1 through the impedance 974 and ground loop to the lead2 through the impedance 972. Note that the loop volume through the lead1 and lead2 at the stimulation site is negligible compared to the loop volume of return paths from ground to lead1 or lead2. This effect is further illustrated in FIG. 24 wherein the canister is not connected to any external ground. As a result, the induced voltage through the circuit 980 is practically non-existent. Thus, from first principles it is shown that the most ideal solution for the blocking of gradient induced voltages is to prevent of gradient induced loops from forming in the first place. This is a direct departure from the notion of blocking the gradient induced voltages in cases wherein, as in traditional designs, the canister ground is connected to the patient tissues. Therefore, in the subsequent sections, the blocking of gradient induced voltages in a conventional implanted device is discussed.

Gradient Blocking in the Case of a Conducting Canister:

A number of different solutions can be provided for blocking the gradient voltages. All these solutions provide a dedicated protective circuit for blocking gradient induced voltages instead of depending on parasitic circuit elements as traditionally done.

Figure 25:
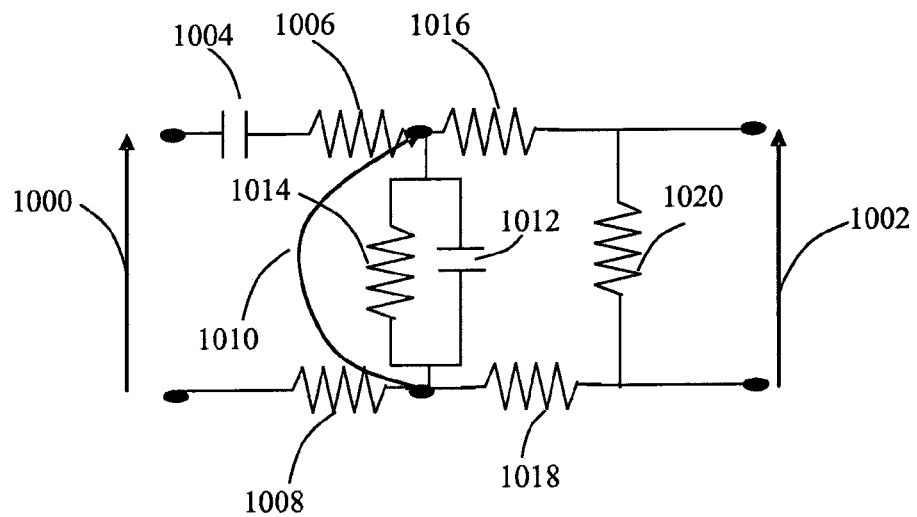
FIG. 25 is the schematic of the gradient induced voltage blocking in a conventional grounded stimulation system with a passive blocking network.

The first exemplary solution is illustrated in FIG. 25 involving a reactive, passive blocking network. In one illustrative example of this kind, passive blocking network may include an optional capacitance 1004 can be provided in series with input resistor 1006 to block very low frequency voltages applied to input 1000. This is essentially like a DC block by a high pass filter. The input 1000 is connected to another input resistor 1008. In any case, a parallel RC network consisting of a resistor 1014 and a capacitor 1012 is provided between leads or between leads and ground to provide transient voltage suppression. Since the RC network is mostly reactive, the energy dissipation is provided by a resistor element 1020, which is connected across the leads or across each lead and the ground. This arrangement can essentially maintain the voltage across 1010 to be approximately the same as across the output 1002. In order for this to be true, as an example, a resistor element 1020 has a resistance that is about 100 times greater than the resistance of either the resistors 1016 and 1018.

Figure 26:
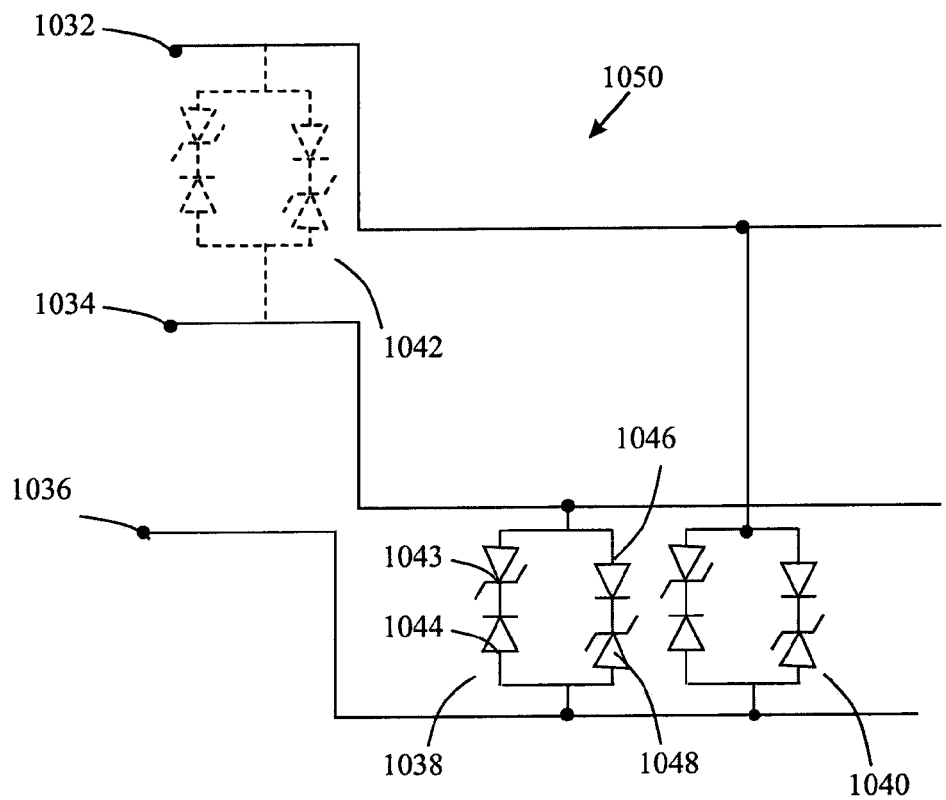
FIG. 26 is the schematic of the gradient induced voltage blocking in a conventional grounded stimulation system with transient voltage suppressor modules.

A second exemplary solution 1050 is illustrated in FIG. 26. This solution makes use of commercially available transient voltage suppressor (TVS) modules. In one exemplary embodiment, a TVS module 1038 may have a first pair of a diode 1044 and a zener diode 1043 arranged back to back in series but in parallel to a second pair of diode 1046 and a zener diode 1048 also arranged back to back in series but in an opposite direction of the first pair. Note that the TVS modules are typically needed between the lead2 1034 and the canister ground 1036 or between the lead1 1032 and the canister ground 1036. Thus, the TVS module 1038 is connected between 1034 and 1036 and the TVS module 1040 is connected between 1032 and 1040. Further note that the TVS module 1042 is shown in dotted lines to illustrate the fact that its use is optional. This is consistent with the earlier discussion where the gradient induced voltage is negligible compared to the ground loops and therefore, typically this module is not used.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. An electrical lead that is adapted for implantation in an animal and compatible with a magnetic resonance imaging scanner, wherein the magnetic resonance imaging scanner responds to signals at a Larmor frequency of tissue in the animal, said electrical lead comprising:
   a first coil including at least one first insulated conductor wound along a length of the lead in a physical manner that defines a first inductance and a first capacitance of the first coil, wherein the first inductance and the first capacitance are configured to cause the first coil to act as a first parallel resonator tuned to the Larmor frequency;
   an electrically conductive layer extending around the first coil; and
   a layer of a material that is electrically insulating and biologically compatible with tissue of the animal, and which forms an external surface of the electrical lead.

2. The electrical lead as recited in claim 1 wherein the first coil comprises a plurality of coiled insulated conductors.

3. The electrical lead as recited in claim 1 wherein the electrically conductive layer contains electrically conductive, non-magnetizable particles in physical contact with each other.

4. The electrical lead as recited in claim 1 wherein the Larmor frequency is one of 64 MHz and 128 MHz.

5. The electrical lead as recited in claim 1 wherein the first coil has the length which is unequal to a multiple of half a wavelength of the Larmor frequency.

6. The electrical lead as recited in claim 1 wherein the at least one first insulated conductor has a conductivity between 1.00 and $2 \times 10^5$ Siemens per meter.

7. The electrical lead as recited in claim 1 further comprising a second coil including at least one second insulated conductor wound along the length of the lead and around the first coil in a physical manner that defines a second inductance and a second capacitance, wherein the second inductance and the second capacitance are configured to cause the second coil to act as a second parallel resonator that resonates at the Larmor frequency.

8. The electrical lead as recited in claim 7 wherein the electrically conductive layer is between the first coil and the second coil.

9. The electrical lead as recited in claim 8 wherein the electrically conductive layer further encases the second coil.

10. The electrical lead as recited in claim 7 wherein the second coil is between the first coil and the electrically conductive layer.

11. The electrical lead as recited in claim 10 further comprising a spacer layer of dielectric material between the first coil and the second coil.

12. The electrical lead as recited in claim 10 further comprising a spacer layer of electrically conductive material between the first coil and the second coil.

13. The electrical lead as recited in claim 7 wherein the first coil and the second coil are wound in identical directions along the length of the lead.

14. The electrical lead as recited in claim 7 wherein the first coil and the second coil are wound in opposite directions along a length of the lead.

15. The electrical lead as recited in claim 7 wherein the first coil and the second coil each comprises a plurality of coiled insulated conductors.

16. The electrical lead as recited in claim 1 wherein the first inductance L is defined by the expression $L=\mu\mu_0 m^2 Al$, where $\mu$ is the magnetic permeability of air, $\mu_0$ is the magnetic permeability of a vacuum, m is the number of turns per unit length of the coil, A is a cross sectional area of the coil, and l is the length of the coil.

17. An electrical lead that is adapted for implantation in an animal and compatible with a magnetic resonance imaging scanner which responds to signals at a Larmor frequency of tissue in the animal, said electrical lead comprising:
- a first plurality of coiled insulated wires wound in a first direction forming an outer layer of conductors, and having a first pitch that produces a first inductance and a first capacitance, wherein the first inductance and the first capacitance are configured to cause the first coil to act as a first parallel resonator tuned to the Larmor frequency;
- a second plurality of coiled insulated wires wound in a second direction forming an inner layer of conductors within the outer layer of conductors, and having a second pitch that produces a second inductance and a second capacitance, wherein the second inductance and the second capacitance are configured to cause the first coil to act as a second parallel resonator tuned to the Larmor frequency;
- an electrically conductive layer extends around the inner layer of conductors; and
- a layer of a material that is biologically compatible with tissue of the animal and extending around the outer layer of conductors and the electrically conductive layer.

18. The electrical lead as recited in claim 17 wherein the electrically conductive layer contains electrically conductive, non-magnetizable particles in physical contact with each other.

19. The electrical lead as recited in claim 17 wherein each of the first plurality of coiled insulated wires and the second plurality of coiled insulated wires has a conductivity between 1.00 and $2\times10^5$ Siemens per meter.

20. The electrical lead as recited in claim 17 wherein the electrically conductive layer is around the outer layer of conductors.

21. The electrical lead as recited in claim 20 further comprising a spacer layer of dielectric material between the inner layer of conductors and the outer layer of conductors.

22. The electrical lead as recited in claim 20 further comprising a spacer layer of electrically conductive material between the inner layer of conductors and the outer layer of conductors.

23. The electrical lead as recited in claim 17 wherein the electrically conductive layer is between the inner layer of conductors and the outer layer of conductors.

24. The electrical lead as recited in claim 17 wherein the first direction and the second direction are identical.

25. The electrical lead as recited in claim 17 wherein the first direction is opposite to the second direction.

26. The electrical lead as recited in claim 17 wherein the coil has a length which is unequal to a multiple of half a wavelength of the Larmor frequency.

27. The electrical lead as recited in claim 17 wherein the first inductance L is defined by the expression $L=\mu\mu_0 m^2 Al$, where $\mu$ is the magnetic permeability of air, $\mu_0$ is the magnetic permeability of a vacuum, m is the number of turns per unit length of the coil, A is the cross sectional area of the coil, and l is the length of the coil.

* * * * *